(12) United States Patent
Kurosaki et al.

(10) Patent No.: US 10,435,189 B2
(45) Date of Patent: Oct. 8, 2019

(54) SEALING APPARATUS FOR CRYOPRESERVATION BAG

(71) Applicant: UEDA SEITAI CO., LTD., Moriguchi-shi, Osaka (JP)

(72) Inventors: Yasuo Kurosaki, Chofu (JP); Katsuhiko Ueda, Moriguchi (JP); Kimitoshi Sato, Tokyo (JP)

(73) Assignee: UEDA SEITAI CO., LTD., Moriguchi-shi, Osaka (JP)

( * ) Notice: Subject to any disclaimer, the term of this patent is extended or adjusted under 35 U.S.C. 154(b) by 643 days.

(21) Appl. No.: 14/787,406

(22) PCT Filed: Feb. 25, 2015

(86) PCT No.: PCT/JP2015/055369
§ 371 (c)(1),
(2) Date: Jul. 5, 2016

(87) PCT Pub. No.: WO2016/024413
PCT Pub. Date: Feb. 18, 2016

(65) Prior Publication Data
US 2016/0304227 A1 Oct. 20, 2016

(30) Foreign Application Priority Data
Aug. 12, 2014 (JP) ................. 2014-164029

(51) Int. Cl.
*B65B 51/22* (2006.01)
*B65B 51/10* (2006.01)
(Continued)

(52) U.S. Cl.
CPC ............ *B65B 51/22* (2013.01); *A01N 1/0263* (2013.01); *B29C 65/16* (2013.01);
(Continued)

(58) Field of Classification Search
CPC . B29C 66/1122; B29C 66/232; B29C 66/244; B29C 66/43; B29C 66/43121;
(Continued)

(56) References Cited

U.S. PATENT DOCUMENTS

| 4,847,462 A | * | 7/1989 | Soodak | ............... B29C 65/7847 219/121.63 |
| 5,049,720 A | * | 9/1991 | Fang | ...................... B23K 26/12 219/121.63 |

(Continued)

FOREIGN PATENT DOCUMENTS

| JP | 2007-302567 A | 11/2007 |
| WO | 2003-039843 A1 | 5/2003 |

OTHER PUBLICATIONS

International Search Report of PCT/JP2015/055369.

*Primary Examiner* — Alexander M Valvis
*Assistant Examiner* — Mary C Hibbert-Copeland
(74) *Attorney, Agent, or Firm* — Muncy, Geissler, Olds & Lowe, P.C.

(57) ABSTRACT

There is provided a sealing apparatus for a cryopreservation bag, with which a sealing treatment of an inlet/outlet of the cryopreservation bag is carried out automatically and anyone can safely and properly carry out the sealing treatment. The sealing apparatus includes: a bag clamping device 56; a laser device 57; and a scanning structure 58 for moving the bag clamping device 56, for example. The bag clamping device 56 includes a fixed pinching block 67, a movable pinching block 69, and a clamp actuator 70. The laser device 57 includes a laser oscillator 104 and a condensing lens 107. The fixed pinching block 67 includes a block base 73, a heat radiator 74, and a heat radiator holder 75. An infrared laser beam is radiated to a sealed portion 55 of the bag to form a seal bead 125 for sealing in a state in which the sealed portion 55 is pinched and fixed by the heat radiator 74 and (Continued)

the movable pinching block 69 and while the bag clamping device 56, for example, is moved by the scanning structure 58.

16 Claims, 14 Drawing Sheets

(51) Int. Cl.
    *B29C 65/16*     (2006.01)
    *B65B 51/14*     (2006.01)
    *A01N 1/02*     (2006.01)
    *B29C 65/78*     (2006.01)
    *B29C 65/00*     (2006.01)
    *B29L 31/00*     (2006.01)

(52) U.S. Cl.
    CPC ...... *B29C 65/1612* (2013.01); *B29C 65/1638* (2013.01); *B29C 65/1654* (2013.01); *B29C 65/7841* (2013.01); *B29C 66/1122* (2013.01); *B29C 66/232* (2013.01); *B29C 66/244* (2013.01); *B29C 66/43121* (2013.01); *B29C 66/71* (2013.01); *B29C 66/73366* (2013.01); *B29C 66/8161* (2013.01); *B29C 66/81261* (2013.01); *B29C 66/81267* (2013.01); *B29C 66/81811* (2013.01); *B29C 66/81831* (2013.01); *B65B 51/10* (2013.01); *B65B 51/146* (2013.01); *B29C 66/43* (2013.01); *B29C 66/8167* (2013.01); *B29C 66/8324* (2013.01); *B29C 66/849* (2013.01); *B29C 66/9672* (2013.01); *B29L 2031/7148* (2013.01)

(58) Field of Classification Search
    CPC .............. B29C 66/71; B29C 66/73366; B29C 66/81261; B29C 66/81267; B29C 66/8161; B29C 66/81811; B29C 65/16; B29C 65/1612; B29C 65/1638; B29C 65/1654; B29C 65/7841; B29C 66/81831; B29C 66/8167; B29C 66/8324; B29C 66/849; B29C 66/9672; B65B 51/22; B65B 51/10; B65B 51/146; A01N 1/0263; B29L 2031/7148
    USPC ..... 53/373, 373.7, 451; 219/121.85, 121.75; 156/272.8, 308.2
    See application file for complete search history.

(56) References Cited

U.S. PATENT DOCUMENTS

| | | | |
|---|---|---|---|
| 9,216,554 B2 * | 12/2015 | Muramatsu | A61J 1/10 |
| 2005/0087456 A1 * | 4/2005 | Oka | A61J 1/2093 |
| | | | 206/219 |
| 2006/0175004 A1 | 8/2006 | Kurosaki et al. | |
| 2007/0034339 A1 * | 2/2007 | Basque | B23K 26/032 |
| | | | 156/515 |
| 2012/0064603 A1 * | 3/2012 | Childs | A01N 1/0252 |
| | | | 435/235.1 |

* cited by examiner

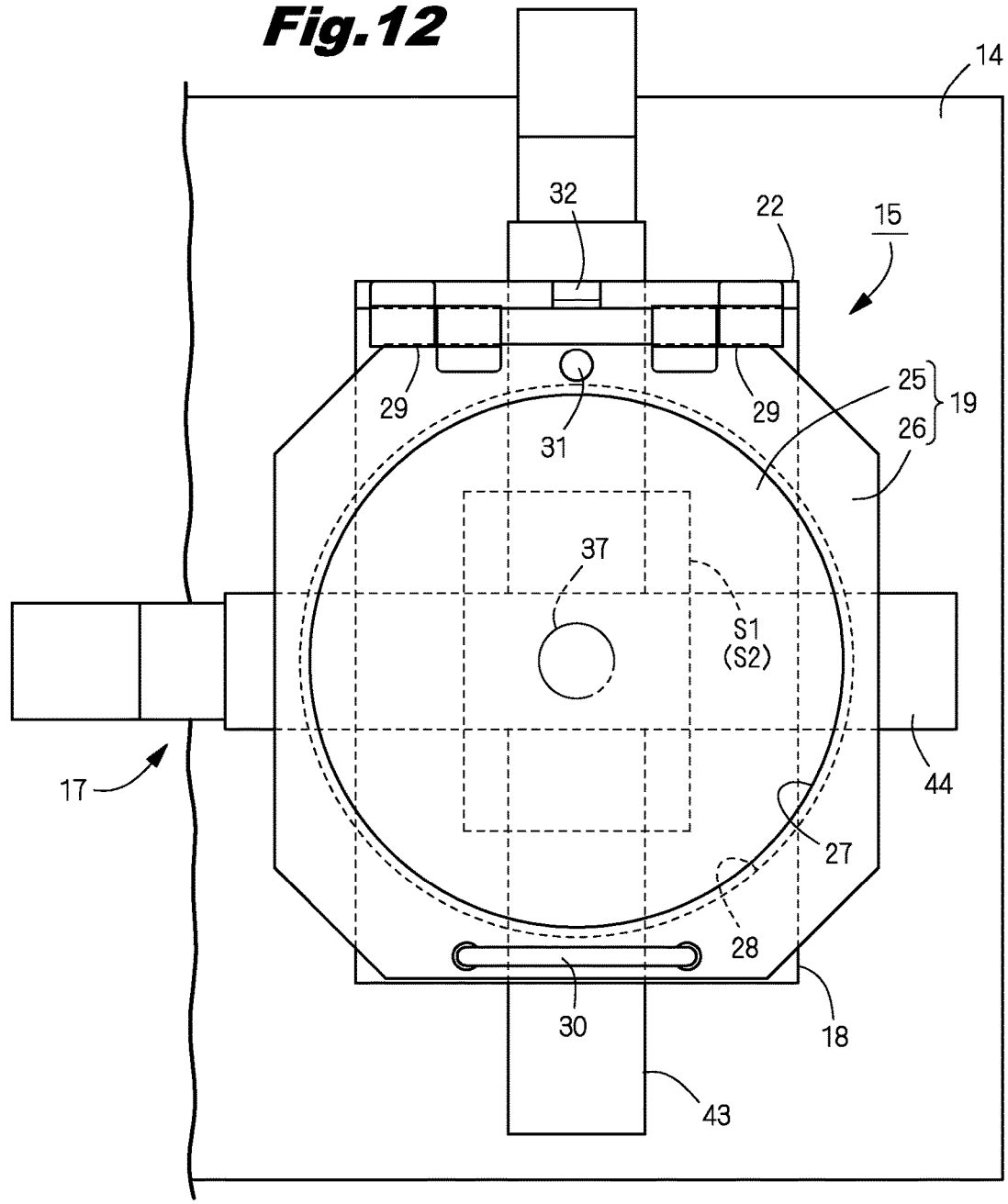

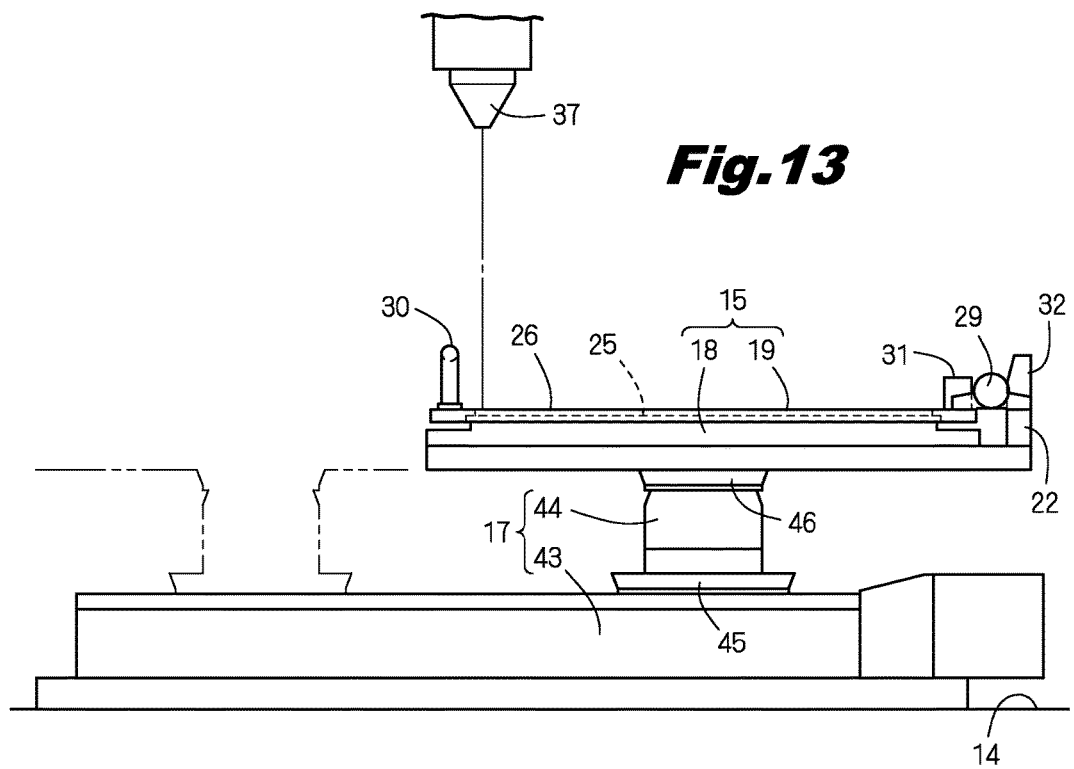
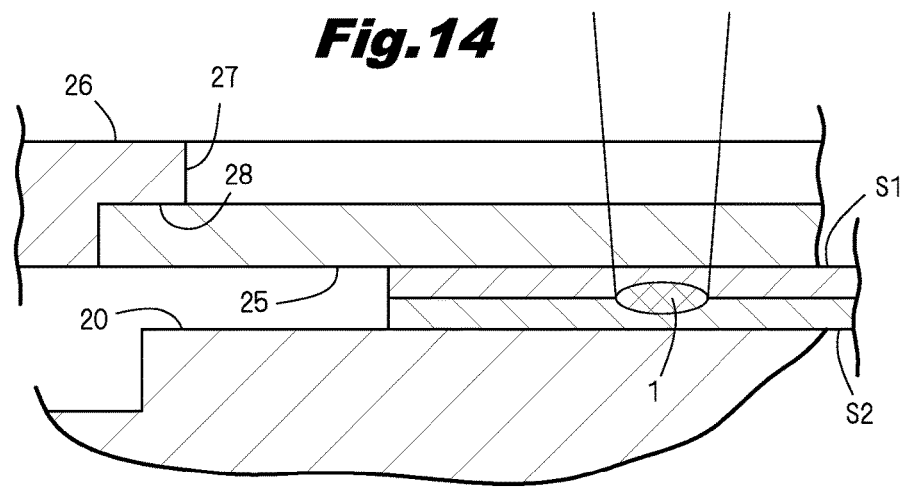

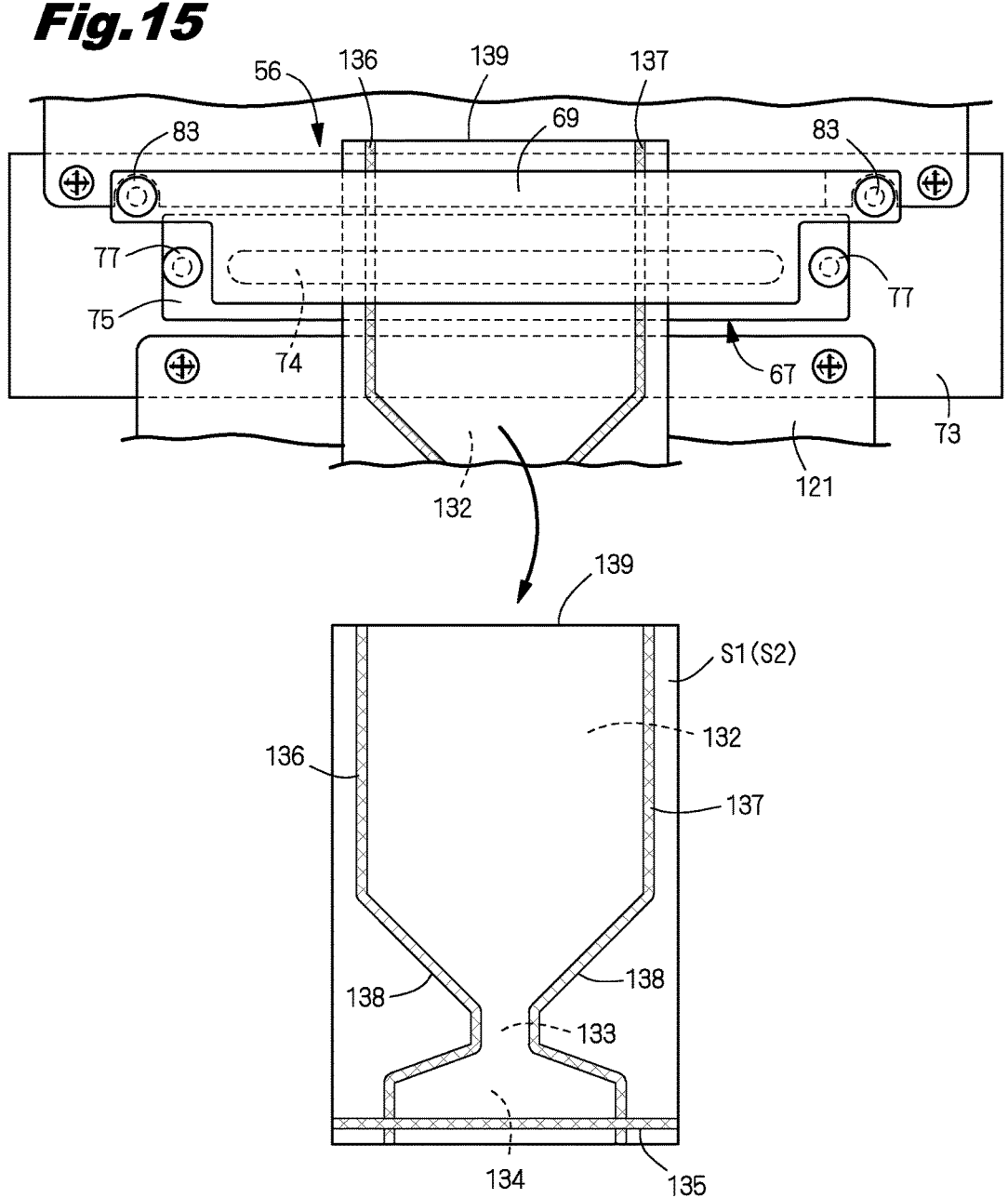

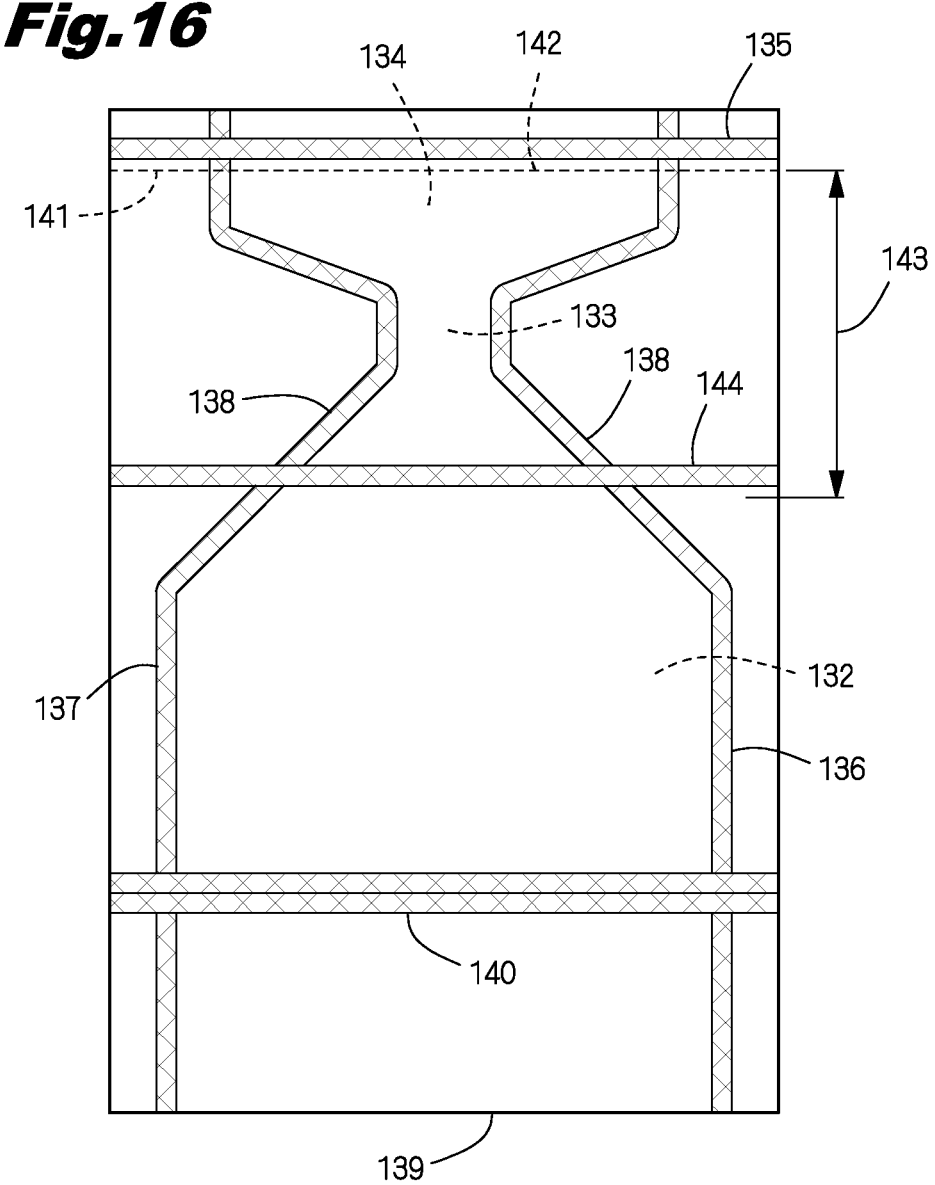

SEALING APPARATUS FOR CRYOPRESERVATION BAG

TECHNICAL FIELD

The present invention relates to a sealing apparatus for sealing and hermetically closing an opening portion of a cryopreservation bag used in cryopreserving human, animal, or plant biological tissue. The cryopreservation bag is formed as a bag-shaped container by welding two layered fluorine-based resin sheets by use of an infrared laser beam.

BACKGROUND ART

This type of cryopreservation bag is disclosed in Patent Literature 1, for example. Here, the bag-shaped cryopreservation bag is formed by sandwiching and pressurizing two layered thermoplastic resin films between a supporter and an infrared transmitting solid heat radiating member (hereinafter merely referred to as "heat radiating member") and radiating an infrared laser beam on both the films from a side of the heat radiating member to form a weld bead.

Regarding the sealing apparatus according to the invention, sealing of an opening portion of a cryopreservation container by thermal welding is disclosed in Patent Literature 2. Here, a plastic container main body for housing a biological sample is integrally provided with an opening portion and a tear portion and the opening portion is sealed by thermal welding with a sealer after the biological sample is housed into the container main body.

PRIOR ART DOCUMENTS

Patent Documents

Patent Document 1: WO 2003/039843 A (page 11, Embodiment 1, FIG. 3)
Patent Document 2: JP 2007-302567 A (column [0035], FIG. 1)

SUMMARY OF THE INVENTION

Problems to be Solved by the Invention

Because the cryopreservation bag in Patent Literature 2 is made of polyethylene terephthalate, for example, the bag can be satisfactorily sealed by use of a commercially available impulse sealer. However, a cryopreservation bag made of fluorine-based resin need be sealed at a higher temperature and therefore it is difficult for the commercially available sealer to uniformly impart a high-level sealing function to every bag by thermally welding an inlet/outlet. Liquid nitrogen may enter the cryopreservation bag which cannot perform the high-level sealing function. If this cryopreservation bag is taken out of a container for liquid nitrogen while the entry is not known, the liquid nitrogen may suddenly expand to break the cryopreservation bag and scatter contents. The cryopreservation bag is often used in clinical settings such as a hospital and doctors and medical technologists who are main users are expected to safely and properly seal the cryopreservation bag and obtain the high-level of sealing function of the bag.

It is an object of the present invention to provide a sealing apparatus for a cryopreservation bag, with which a sealing treatment of the cryopreservation bag can be carried out easily, automatically, safely, and properly.

Solution to Problems

A sealing apparatus for a cryopreservation bag according to a first aspect of the present invention includes: a bag clamping device 56 for pinching and fixing a sealed portion 55 of the cryopreservation bag; a laser device 57 for radiating an infrared laser beam toward the sealed portion 55 pinched and fixed by the bag clamping device 56; a scanning structure 58 for moving any one of the bag clamping device 56 and the laser device 57; and a frame 59 for supporting the respective members 56 to 58. The bag clamping device 56 includes a fixed pinching block 67 supported by a scanning base 65 fixed to the frame 59, a movable pinching block 69 supported by a guide shaft 68 provided to the fixed pinching block 67 to be able to come in contact with and move away from the fixed pinching block 67, and a clamp actuator 70 for bringing the movable pinching block 69 into contact with and moving the movable pinching block 69 away from the fixed pinching block 67. The laser device 57 includes a laser oscillator 104 and a condensing lens 107 for condensing the infrared laser beam radiated from the laser oscillator 104 toward the sealed portion 55 of the cryopreservation bag. The fixed pinching block 67 includes a block base 73 in which a radiation window 72 for the infrared laser beam is open, a heat radiator 74 made of solid material with high infrared transmissivity and high heat conductivity, and a heat radiator holder 75 mounted to the block base 73 to support the heat radiator 74 so that the heat radiator 74 faces the radiation window 72. The infrared laser beam is radiated to the sealed portion 55 of the cryopreservation bag to form a seal bead 125 crossing an inlet/outlet 3 at the sealed portion 55 in a state in which the sealed portion 55 is pinched and fixed by the heat radiator 74, the heat radiator holder 75, and the movable pinching block 69 and while any one of the bag clamping device 56 and the laser device 57 is moved by the scanning structure 58.

The scanning structure 58 includes a guide body 89 provided to the scanning base 65, a slide body 90 guided and supported by the guide body 89 to be able to slide leftward and rightward, a clamping table 91 fixed to the slide body 90, and a scanning actuator 93 provided to the scanning base 65 to reciprocate the clamping table 91 leftward and rightward. The block base 73 of the fixed pinching block 67 is supported by the clamping table 91. The infrared laser beam is radiated from the radiation window 72 to the sealed portion 55 to form the seal bead 125 crossing the inlet/outlet 3 at the sealed portion 55 while the bag clamping device 56 is moved by the scanning structure 58.

The scanning base 65 is fixed to an upper frame 60 forming the frame 59. A scanning window 66 for allowing leftward and rightward movements of the bag clamping device 56 is open in the scanning base 65 and the movable pinching block 69 and the fixed pinching block 67 face an outer face of the scanning window 66. The sealed portion 55 of the cryopreservation bag can be attached to and detached from the bag clamping device 56 on the outer face of the scanning window 66.

The movable pinching block 69 is supported by paired left and right sliders 79 supported by the guide shaft 68 to be able to slide forward and backward in a reciprocating manner, a plate-shaped movable base 80 fixed to and supported by both the sliders 79, and paired left and right block support shafts 81 fixed to left and right positions of a front face of the movable base 80. The clamp actuator 70 for moving the movable pinching block 69 forward and backward via the movable base 80 and the block support shafts 81 is provided to an inner base 84 fixed to the guide shaft 68.

The sealed portion 55 of the cryopreservation bag is clamp-fixed by both the fixed and movable pinching blocks 67 and 69 by operating the movable pinching block 69 with the clamp actuator 70 in a state in which the sealed portion 55 is brought in contact with an outer face of the heat radiator 74 of the fixed pinching block 67.

The movable pinching block 69 is detachably mounted to a block support shaft 81 by a first mounting member 83. The heat radiator holder 75 is detachably mounted to the block base 73 by a second mounting member 77. The movable pinching block 69 and the heat radiator holder 75 can be detached from the block support shaft 81 and the block base 73 and sterilized.

A focus adjustment structure for adjusting a focus position of the condensing lens 107 is provided inside the frame 59. The focus adjustment structure includes a lens base 108 supported by an inner frame 92 fixed to the scanning base 65, a lens guide 109 fixed to the lens base 108, a forward-backward slider 110 supported by the lens guide 109 to be able to slide forward and backward, a lens holder 111 fixed to the forward-backward slider 110 to support the condensing lens 107, and a focus adjustment actuator 112 for operating the lens holder 111 forward and backward. The focus position of the condensing lens 107 is adjusted according to a thickness of the sealed portion 55 pinched and fixed by the bag clamping device 56.

A vertical scanning structure for adjusting a vertical position of the bag clamping device 56 is provided inside the frame 59. The vertical adjustment structure includes a vertical guide 97 fixed to the clamping table 91, a vertical slider 98 fixed to the block base 73 and supported by the vertical guide 97 to be able to slide vertically, an actuator base 100 fixed to the clamping table 91, and a vertical scanning actuator 99 disposed between the base 100 and the inner base 84 to operate the bag clamping device 56 vertically. A position of the sealed portion 55 where the seal bead 125 is formed can be changed by vertically operating the bag clamping device 56 with the vertical scanning structure.

A moving stroke of the bag clamping device 56 by the scanning structure 58 is set to be larger than a left-right width of the sealed portion 55 of the cryopreservation bag and the seal bead 125 can be formed across the sealed portion 55 of the cryopreservation bag from one end to the other end.

An outer face of the frame 59 is covered with a protective barrier 117 for preventing exposure to infrared laser leaking from the laser device 57. A protective cover 118 for preventing exposure to the infrared laser is provided to an outer face of the bag clamping device 56 to be able to open and close.

Advantageous Effects of Invention

The sealing apparatus for the cryopreservation bag according to the first aspect of the invention is formed by the bag clamping device 56, the laser device 57, the scanning structure 58, and the like. The bag clamping device 56 is formed by the fixed pinching block 67, the movable pinching block 69, the clamp actuator 70 for bringing the fixed pinching block 67 and the movable pinching block 69 into contact with each other and moving them away from each other, and the like so that the sealed portion 55 of the cryopreservation bag can be pinched and fixed by both the pinching blocks 67 and 69 by actuating the actuator 70. Furthermore, the fixed pinching block 67 is formed by the block base 73, the heat radiator 74, the heat radiator holder 75, and the like so that the infrared laser beam throttled by the condensing lens 107 can be radiated to the sealed portion 55 through the heat radiator 74 to form the seal bead 125 while any one of the bag clamping device 56 and the laser device 57 is moved by the scanning structure 58.

With the above-described sealing apparatus, the inlet/outlet 3 of the cryopreservation bag formed by fluorine-based resin sheets S1 and S2 can be sealed easily and automatically by moving the movable pinching block 69 by the clamp actuator 70 to clamp the sealed portion 55 and then actuating the scanning structure 58 and the laser device 57. The sealing operation of the sealed portion 55 of the cryopreservation bag is carried out by doctors or medical technologists. Because a series of welding operations is carried out automatically after the sealed portion 55 is clamped by the bag clamping device 56, it is possible to safely and properly carry out the sealing treatment of the cryopreservation bag. Moreover, the sealing treatment is always carried out automatically under constant conditions and therefore there is no variation between welding results. As a result, it is possible to provide the sealing apparatus for the cryopreservation bag, with which anyone can easily carry out the sealing treatment which can stably impart the high sealing function. Especially, the sealing treatment can be carried out properly even for the cryopreservation bag made of fluorine-based resin which need be sealed at a high temperature.

If the scanning window 66 for allowing the leftward and rightward movements of the bag clamping device 56 is open in the scanning base 65 and the movable pinching block 69 and the fixed pinching block 67 face the outer face of the scanning window 66, it is possible to easily attach and detach the sealed portion 55 to and from the bag clamping device 56 on the outer face of the scanning window 66. Therefore, it is possible to appropriately clamp the sealed portion 55 with the bag clamping device 56 while checking a position and an attitude of the cryopreservation bag or it is possible to reliably retrieve the cryopreservation bag after the welding operation is finished, which improves usability of the sealing apparatus.

If the movable pinching block 69 is supported by the paired sliders 79, the movable base 80, and the paired block support shafts 81 fixed to the movable base 80 to be able to slide forward and backward with respect to the guide shaft 68 of the fixed pinching block 67, the movable pinching block 69 can be smoothly moved forward and backward with respect to the fixed pinching block 67 and parallelism between pinching faces of both the pinching blocks 67 and 69 can be enhanced. Moreover, if the clamp actuator 70 is provided to the inner base 84 fixed to the guide shaft 68, the movable pinching block 69 can be operated forward and backward by the clamp actuator 70 with the simpler structure and the sealed portion 55 can be reliably clamp-fixed between both the fixed and movable pinching blocks 67 and 69.

The movable pinching block 69 is detachably mounted to the block support shaft 81 by the first mounting member 83. The heat radiator holder 75 is detachably mounted to the block base 73 by the second mounting member 77. With this sealing apparatus, the movable pinching block 69 and the heat radiator holder 75 can be detached from the block support shaft 81 and the block base 73 as necessary and the movable pinching block 69 and the heat radiator holder 75 to which the biological tissue may be attached can be sterilized. Therefore, it is possible to facilitate hygiene control of the movable pinching block 69, the heat radiator 74, and the heat radiator holder 75 to carry out the sealing treatment of the sealed portion 55 of the cryopreservation bag in a hygienically safe condition.

If the focus adjustment structure for adjusting the focus position of the condensing lens 107 is provided, the focus position of the condensing lens 107 can be easily adjusted by only actuating the focus adjustment actuator 112. Therefore, the sealed portion 55 can be welded under optimum welding conditions by adjusting the focus position of the condensing lens 107 according to differences in material and thickness of the fluorine-based resin sheets S1 and S2 forming the cryopreservation bag.

If the vertical scanning structure for adjusting the vertical position of the bag clamping device 56 is provided, a position of the sealed portion 55 to be welded can be changed easily in a vertical direction by actuating the vertical scanning actuator 99. Moreover, by actuating the vertical scanning actuator 99 in synchronization with a feeding operation of the scanning structure 58, it is possible to diversify patterns in which the seal bead 125 is formed, e.g., multiple seal beads 125 may be formed or the seal bead 125 may be formed in a continuous wave pattern.

If the moving stroke of the bag clamping device 56 by the scanning structure 58 is set to be larger than the lateral width of the sealed portion 55 of the cryopreservation bag, the seal bead 125 can be formed continuously from one end to the other end of the sealed portion 55. Therefore, it is possible to obtain the cryopreservation bag in which the sealed portion 55 is more reliably sealed with the continuous seal bead 125 and which has sufficient durability to withstand severe cryopreservation.

If the outer face of the frame 59 is covered with the protective barrier 117 and the protective cover 118 which can open and close is provided to the outer face of the bag clamping device 56, it is possible to prevent a user from being exposed to the infrared laser leaking from the laser device 57 in welding of the sealed portion 55 and therefore the sealing treatment of the sealed portion 55 can be carried out further safely.

BRIEF DESCRIPTION OF THE DRAWINGS

FIG. 12 is a front view of the manufacturing device of the cryopreservation bag.

FIG. 13 is a side view showing movement of an operating structure.

FIG. 14 is a sectional view showing a condition in which a weld bead is formed.

FIG. 15 is a front view showing a variation of the cryopreservation bag.

FIG. 16 is a front view showing a sealing structure of the cryopreservation bag in FIG. 15.

DESCRIPTION OF EMBODIMENTS

FIGS. 1 to 14 show embodiments of a sealing apparatus and related devices for a cryopreservation bag according to the invention. Front, back, left, right, up, and down in the invention are shown by four-direction arrows shown in FIGS. 2 and 3 and words, front, back, left, right, up, and down written near the respective arrows. The sealing apparatus according to the invention seals the cryopreservation bag having a structure shown in FIG. 8, for example. Before describing the sealing apparatus, the structure of the cryopreservation bag and a manufacturing device of the bag will be described briefly.

Figure 8:
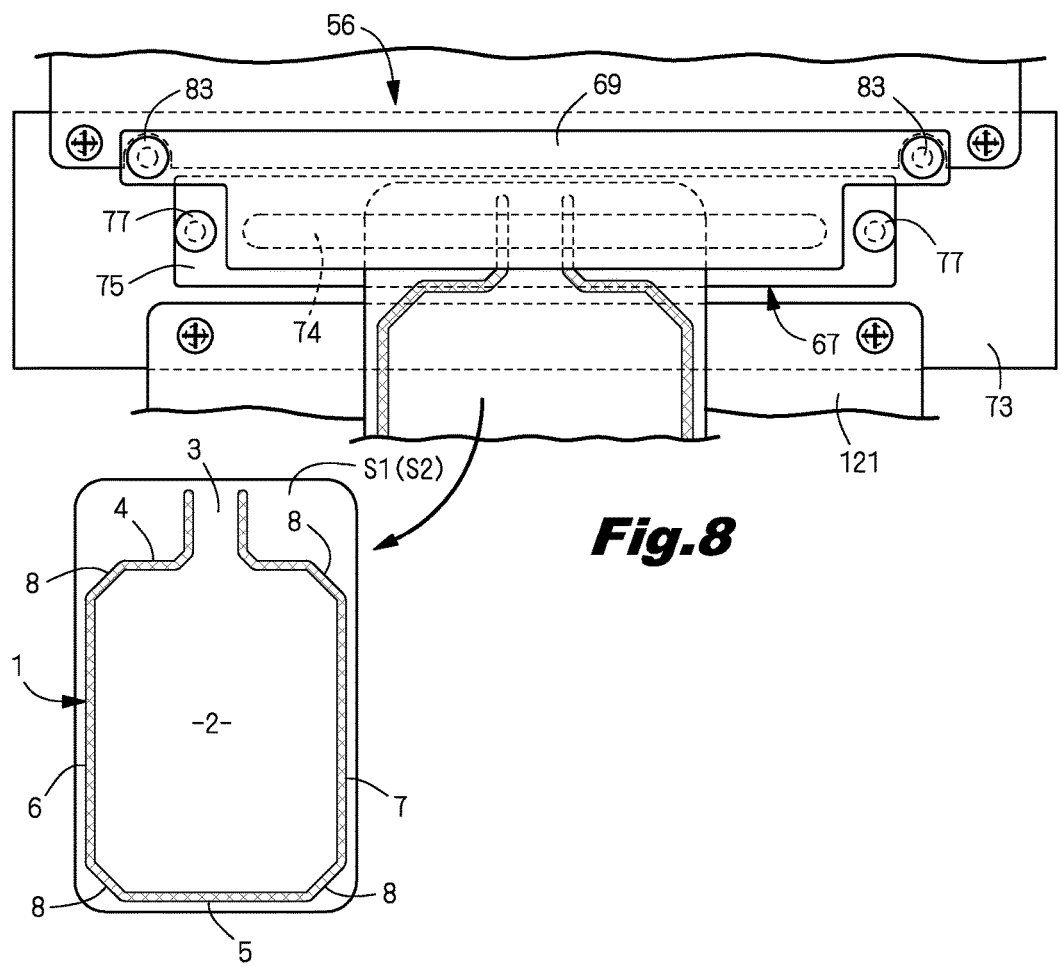
FIG. 8 is a front view showing the procedure for attaching the sealed portion to the bag clamping device.

In FIG. 8, the cryopreservation bag is obtained by forming a traversable outline bead 1 at an interface between two layered fluorine-based resin sheets S1 and S2 by radiating an infrared laser beam on the sheets S1 and S2 to form a housing portion 2 in which biological tissue is to be housed and an inlet/outlet 3 continuous with the housing portion 2 in an area between both the sheets S1 and S2 and surrounded with the outline bead 1. The outline bead 1 defining the housing portion 2 is formed by paired parallel upper bead portion 4 and lower bead portion 5, paired parallel left bead portion 6 and right bead portion 7, and four corner bead portions 8 formed at corner portions adjacent to the respective bead portions 4 to 7. In this way, the housing portion 2 is formed into a vertically-long rectangular shape with four rounded corners. The inlet/outlet 3 is formed at a center in a left-right direction of the upper bead portion 4. By providing the corner bead portions 8, right-angled inner corners are not formed in the housing portion 2 and the biological tissue housed in the housing portion 2 can be taken out until nothing is left.

The fluorine-based resin sheets S1 and S2 are formed as infrared laser transmitting transparent sheets made of any one of perfluorinated resin, partially fluorinated resin, and fluorinated resin copolymer. Specifically, the materials may be polytetrafluoroethylene (PTFE), polychlorotrifluoroethylene (PCTFE), polyvinylidene fluoride (PVDF), polyvinyl fluoride (PVF), perfluoroalkoxy fluorine-based resin (PFA), tetrafluoroethylene-hexafluoropropylene copolymer (FEP), ethylene-tetrafluoroethylene copolymer (ETFE), chlorotrifluoroethylene copolymer (ECTFE), and the like. In the embodiment, the fluorine-based resin sheets S1 and S2 are formed by the sheets made of tetrafluoroethylene-hexafluoropropylene copolymer and having thicknesses of 100 μm and both the sheets S1 and S2 are irradiated with the infrared laser beam to form the cryopreservation bag.

Figure 11:
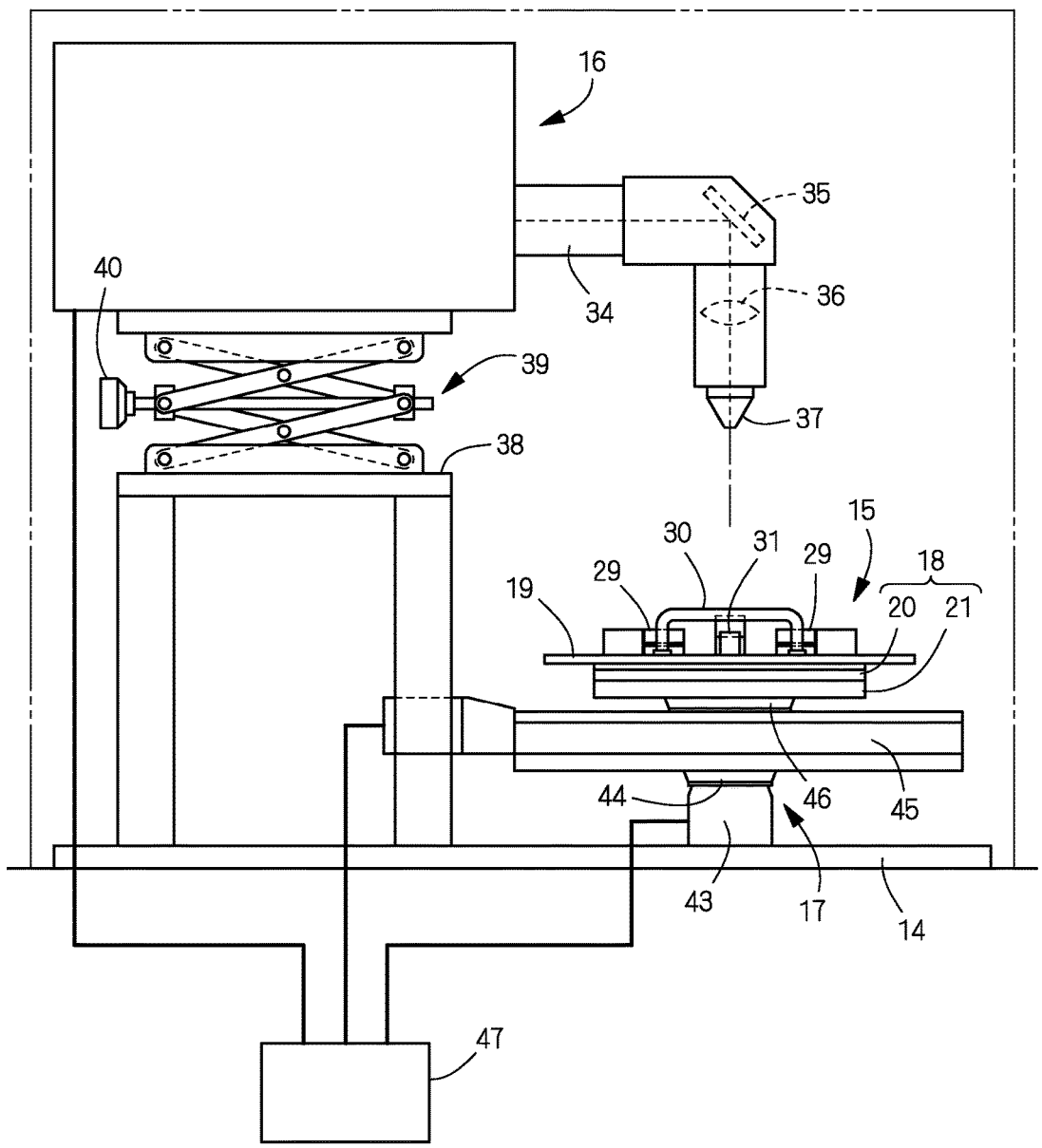
FIG. 11 is a schematic front view of the manufacturing device of the cryopreservation bag.

In FIG. 11, the manufacturing device for the cryopreservation bag is formed by a sheet fixing structure 15 on a base 14, a laser device 16 for radiating the infrared laser beam toward the two layered fluorine-based resin sheets S1 and S2 supported by the sheet fixing structure 15, a scanning structure 17 for moving the sheet fixing structure 15 with respect to the infrared laser beam, and the like.

The sheet fixing structure 15 is formed by a sheet table 18 for supporting the two layered fluorine-based resin sheets S1 and S2 and a sheet pressing body 19 for pressing and retaining the fluorine-based resin sheets S1 and S2 placed on the sheet table 18. The sheet table 18 includes an aluminum table main body 20 having high heat conductivity and a table base 21 for fixing and supporting the table main body 20 and a bracket 22 to which hinges 29 (described later) are mounted on left and right sides of a back end of the table base 21 is formed to protrude upward (see FIG. 10). An upper face (placing face) of the table main body 20 on which the fluorine-based resin sheets S1 and S2 are placed is formed as a flush horizontal face.

The sheet pressing body 19 includes a heat radiator 25 made of solid material having high infrared transmissivity and heat conductivity and a steel pressing frame 26 for supporting the heat radiator 25. The heat radiator 25 is formed by a single-crystal silicon disc transparent to the infrared laser. As shown in FIG. 12, the pressing frame 26 is formed by an octagon-shaped metal frame body, a circular laser window 27 is open at a center of the pressing frame 26, and a circular mounting seat 28 is formed on a lower face side of the window 27. The heat radiator 25 is fitted and fixed into the mounting seat 28.

By connecting a back portion of the pressing frame 26 and the bracket 22 of the table base 21 with the paired left and right hinges 29, the entire sheet pressing body 19 is supported on the sheet table 18 to be able to swing open and close in a vertical direction. The sheet pressing body 19 can be displaced between a welding attitude shown in FIGS. 12 and 13 and a standby attitude shown in FIG. 10 when a handle 30 is gripped and opened/closed. A stopper 32 fixed to the bracket 22 receives a rubber block 31 provided at a center of the back portion of the sheet pressing body 19 so as to retain the sheet pressing body 19, which has been opened into the standby attitude, in a backward inclined attitude. In this state, the two layered fluorine-based resin sheets S1 and S2 are placed on the table main body 20 or a blank body of the cryopreservation bag after the welding treatment can be taken out of the table main body 20.

The laser device 16 is a commercially available carbon dioxide laser unit, a radiating pipe 34 protrudes from a side end of a rectangular box-shaped case which is long in a left-right direction, and a laser beam output from a resonator in the case is deflected downward by a deflecting mirror 35 and then throttled by a condensing lens 36 provided in a laser head and radiated from a laser nozzle 37. The laser device 16 is supported by a laser base 38 fixed onto the base 14 and a height adjustment structure 39 provided to the laser base 38. The height adjustment structure 39 is formed by assembling a plurality of pairs of linkages in X shapes and a vertical height of the laser device 16 can be adjusted by increasing and decreasing angles of intersection of the X-shaped pairs of linkages by turning an adjustment threaded shaft 40 disposed at a center in a vertical direction of the linkage pairs.

The scanning structure 17 is formed as an X-Y stage by a Y-axis slider 43 fixed onto the base 14 and an X-axis slider 44 fixed to a moving table 45 of the Y-axis slider 43. The Y-axis slider 43 and the X-axis slider 44 are respectively formed by commercially available ball screw type electric sliders and disposed to be orthogonal to each other. The table base 21 of the sheet table 18 is fixed to a moving table 46 of the X-axis slider 44. By supporting the table base 21 on the X-Y stage provided to the base 14, it is possible to freely displace the table main body 20 with respect to the laser nozzle 37. In this way, by radiating the infrared laser beam on the fluorine-based resin sheets S1 and S2 while moving the moving tables 45 and 46 of the Y-axis slider 43 and the X-axis slider 44 according to preset X-Y coordinates, it is possible to form a weld bead in an arbitrary shape in the interface between both the sheets S1 and S2. In FIG. 11, reference sign 47 designates a controller for controlling actuated states of the laser device 16 and the scanning structure 17.

Figure 10:
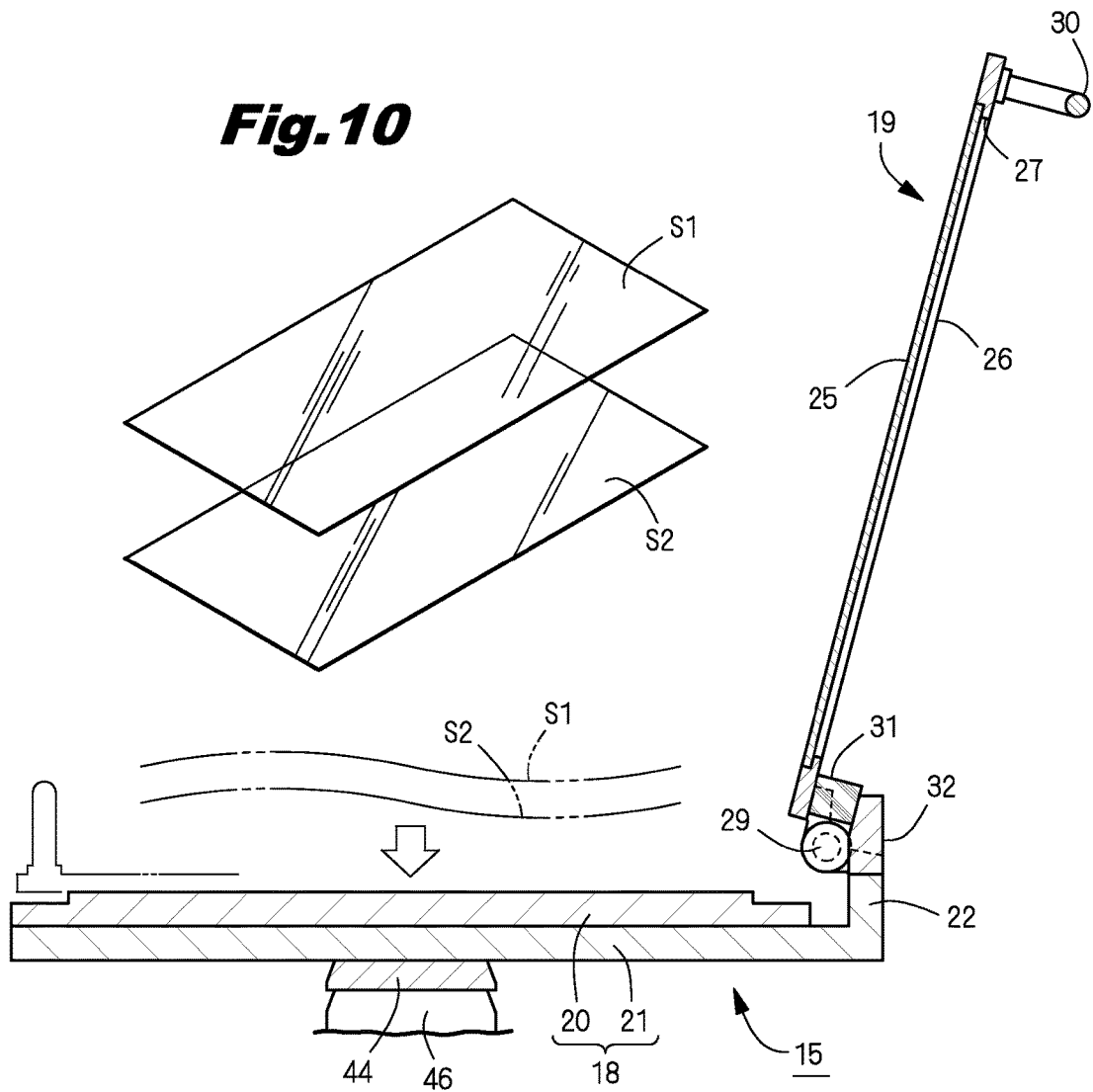
FIG. 10 is a vertical sectional side view of a manufacturing device of the cryopreservation bag according to the invention.

The cryopreservation bag is manufactured by the following manufacturing procedure. The laser device 16 carries out focus adjustment of its condensing lens 36 in advance so that the infrared laser beam is focused on the interface between the two layered fluorine-based resin sheets S1 and S2. After the sheet pressing body 19 is opened into the standby attitude as shown in FIG. 10, the fluorine-based resin sheets S1 and S2 are placed and positioned at a center of the table main body 20 and the sheet pressing body 19 is swung down into the welding attitude. Then, as shown in FIG. 13, the scanning structure 17 is actuated to align a welding start position with a radiation position of the infrared laser beam and the traversable outline bead 1 is formed in the interface between the fluorine-based resin sheets S1 and S2 while the laser device 16 and the scanning structure 17 are actuated synchronously.

In FIGS. 1 to 9, the sealing apparatus for the cryopreservation bag is formed by a bag clamping device 56 for pinching and fixing a sealed portion 55 (see FIG. 9) of the cryopreservation bag, a laser device 57 for radiating the infrared laser beam toward the sealed portion 55 pinched and fixed by the bag clamping device 56, a scanning structure 58 for moving the bag clamping device 56, a frame 59 for supporting the respective members 56 to 58, and the like. The frame 59 includes an upper frame 60 to which the bag clamping device 56, the scanning structure 58, and the like are mounted and a lower frame 61 for supporting the upper frame 60 and the laser device 57 and a controller 62 are disposed inside the lower frame 61. A scanning base 65 in a laterally-long plate shape is fixed to an inner face of a backward-inclining front portion of the upper frame 60 and a scanning window 66 for allowing leftward and rightward movements of the bag clamping device 56 is open at the center in a vertical direction of the scanning base 65.

Figure 9:
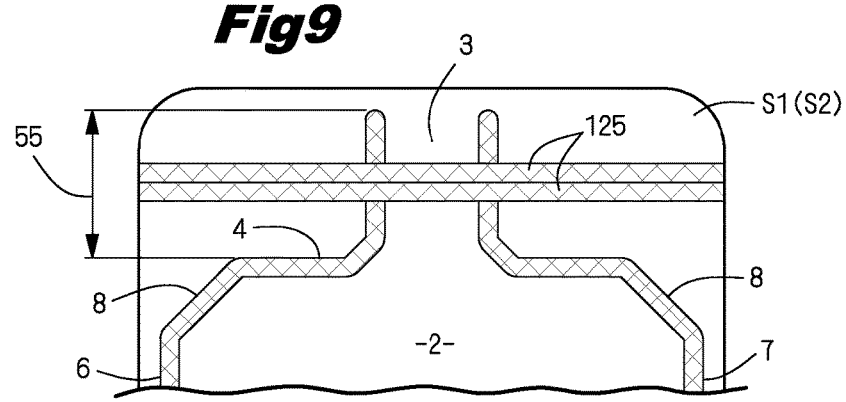
FIG. 9 is a front view showing an example of forming of seal beads.

As described already, after the biological tissue is filled into the housing portion 2 of the cryopreservation bag and the bag is evacuated, seal beads 125 (described later) are formed at the sealed portion 55 to be orthogonal to the inlet/outlet 3. As shown in FIG. 9, the sealed portion 55 is a sheet area between the upper bead portion 4 and an upper end of the inlet/outlet 3 and the seal beads 125 are preferably formed to be orthogonal to or to intersect the inlet/outlet 3 at the center in the vertical direction of the sealed portion 55.

Figure 1:
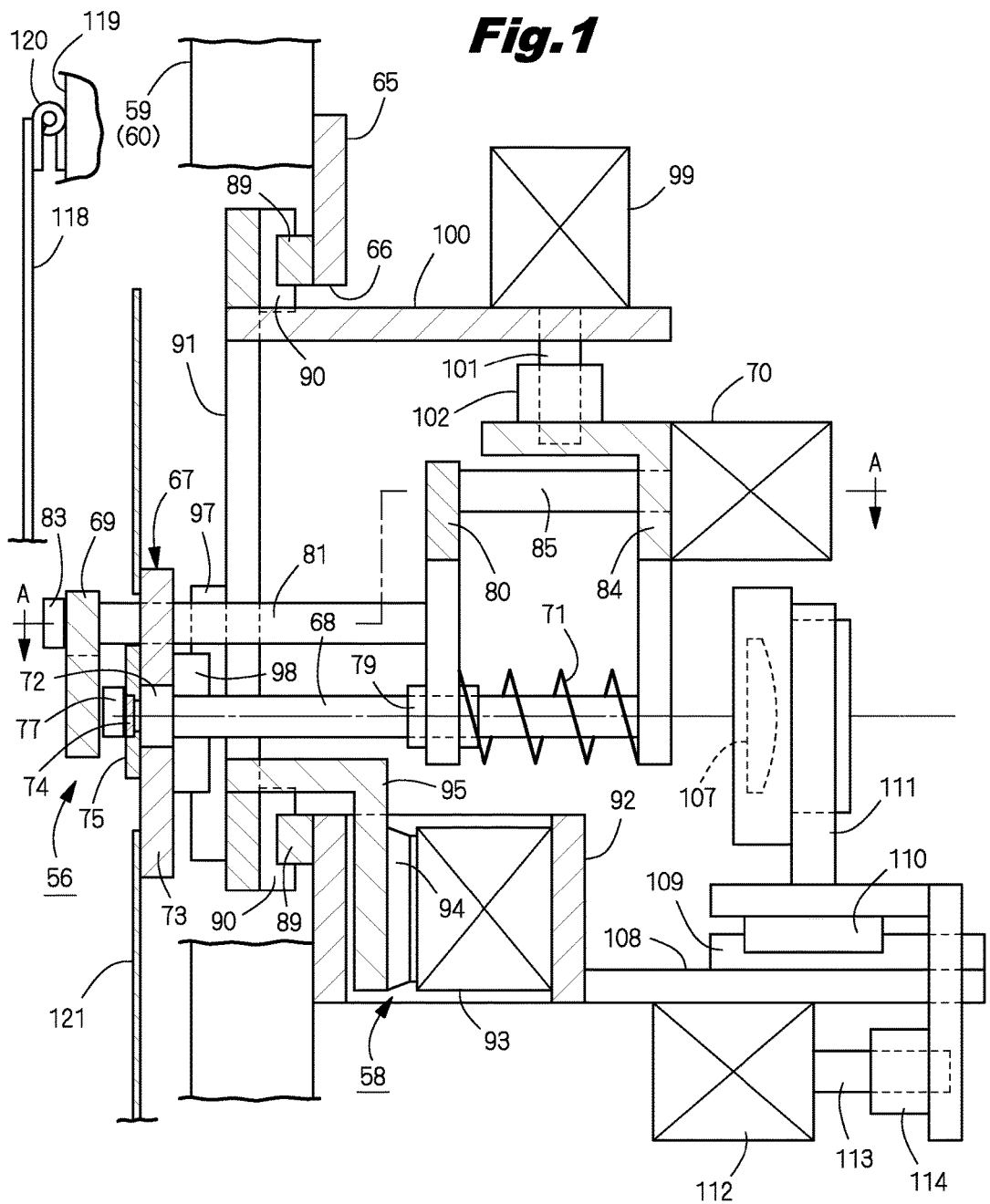
FIG. 1 is a vertical sectional side view of a main part of a sealing apparatus of a cryopreservation bag according to the present invention.
Figure 4:
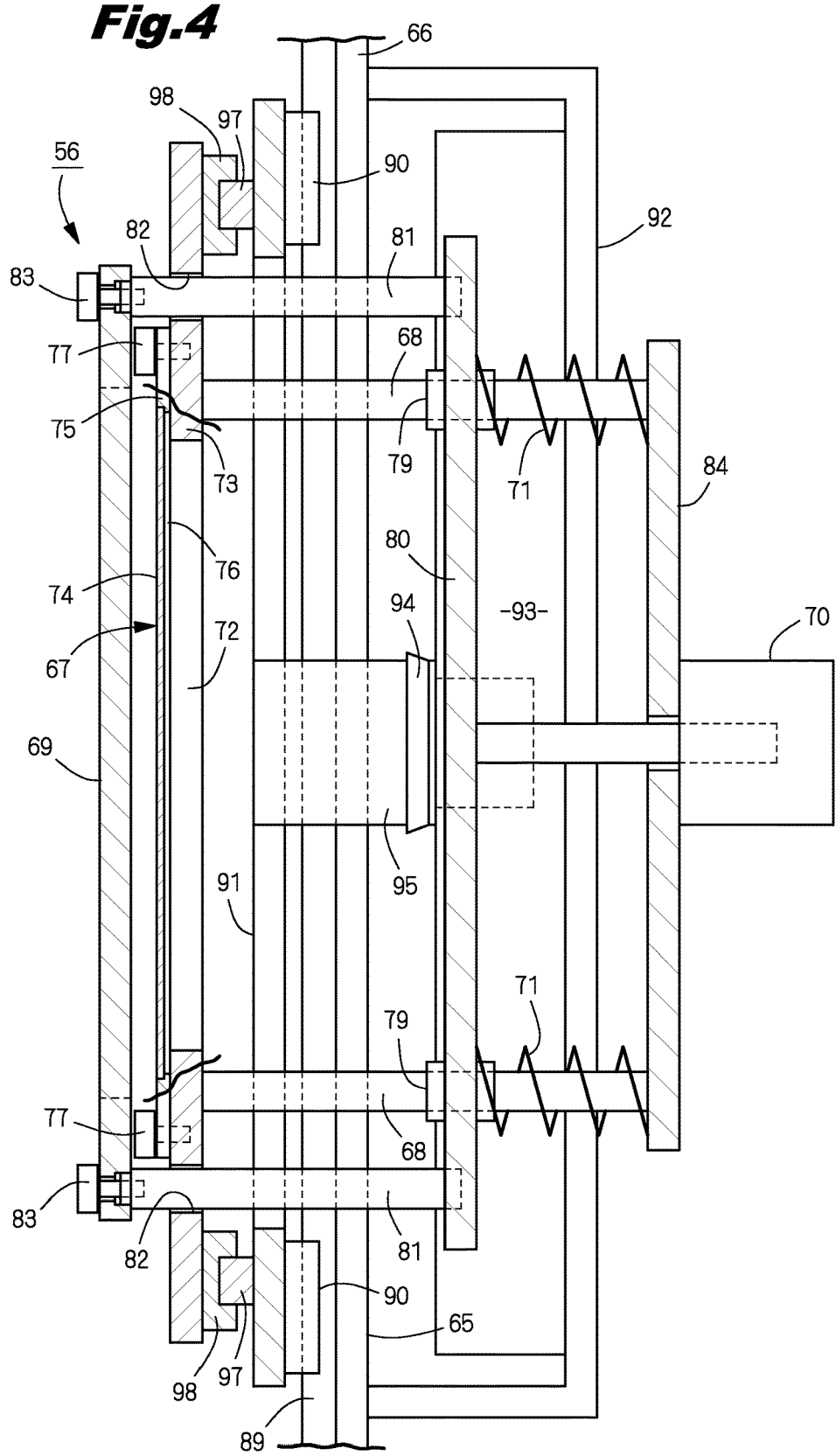
FIG. 4 is a sectional view taken along line A-A in FIG. 1.
Figure 5:
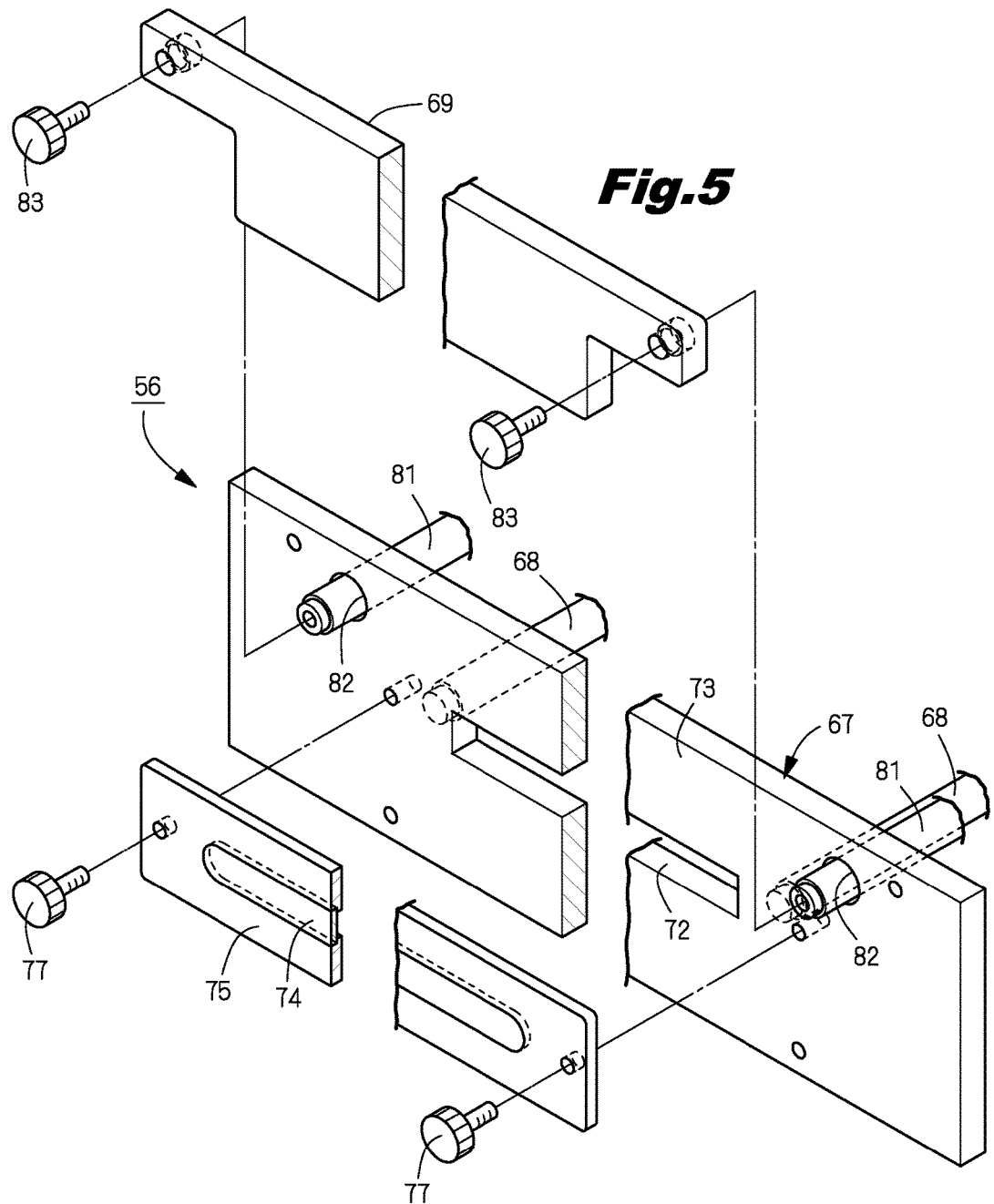
FIG. 5 is an exploded perspective view of a bag clamping device.

In FIGS. 1, 4, and 5, the bag clamping device 56 is formed by a fixed pinching block 67 supported by the scanning base 65, a movable pinching block 69 supported by paired guide shafts 68 fixed to a back face of the fixed pinching block 67 to be able to come in contact with and move away from the fixed pinching block 67, a solenoid (clamp actuator) 70 (see FIG. 1) for bringing the movable pinching block 69 in contact with and moving the movable pinching block 69 away from the fixed pinching block 67, compression coil springs 71 for moving and biasing the movable pinching block 69 forward, and the like. The fixed pinching block 67 includes a block base 73 which is long in the left-right direction and in which a radiation window 72 for the infrared laser beam is open, a heat radiator 74 made of solid material having high infrared transmissivity and heat conductivity and a heat radiator holder 75 mounted to the block base 73 to support the heat radiator 74 so that the heat radiator 74 faces the radiation window 72.

The block base 73 of the fixed pinching block 67 is supported by a clamping table 91 and a vertical adjustment structure and this will be described later in detail. The heat radiator 74 is made of solid material having high infrared transmissivity and heat conductivity. As the solid material forming the heat radiator 74, any one of zinc selenide, zinc sulfide, and silicon, which are transparent to the infrared laser, can be used, because the welding treatment is carried out by use of the carbon dioxide laser. In the embodiment, the heat radiator 74 is formed in a laterally-long plate shape by using single-crystal silicon. The heat radiator 74 is mounted and fixed to the heat radiator holder 75 so as to close a front face of a radiation slit 76 open at a center in the vertical direction of the heat radiator holder 75 made of steel. Front faces of the heat radiator 74 and the heat radiator holder 75 are flush with each other. Left and right opposite ends of the heat radiator holder 75 are detachably mounted by second screw bodies (second mounting members) 77 screwed into the block base 73 (see FIG. 4). The second screw bodies 77 are hand screws, each formed by fixing an operating knob to an end portion of a threaded shaft, and it is possible to mount and detach the heat radiator holder 75 by turning the operating knob with fingertips.

The movable pinching block 69 is formed by an aluminum plate material having high heat conductivity and supported by paired left and right sliders 79 supported by the above-described guide shafts 68 to be able to slide in reciprocating manners, a plate-shaped movable base 80 fixed to and supported by both the sliders 79, and paired left and right block support shafts 81 fixed to left and right positions of a front face of the movable base 80 as shown in FIG. 1. The block support shafts 81 protrude forward from shaft insertion holes 82 (see FIG. 4) formed in the block base 73 and the movable pinching block 69 is detachably mounted to front ends of the block support shafts 81 by first screw bodies (first mounting members) 83. The first screw bodies 83 are hand screws similar to the second screw bodies 77. In order to make attachment and detachment of the sealed portion 55 by the bag clamping device 56 easy and reliable, the movable pinching block 69 and the fixed pinching block 67 respectively face an outer face of the scanning window 66.

Figure 2:
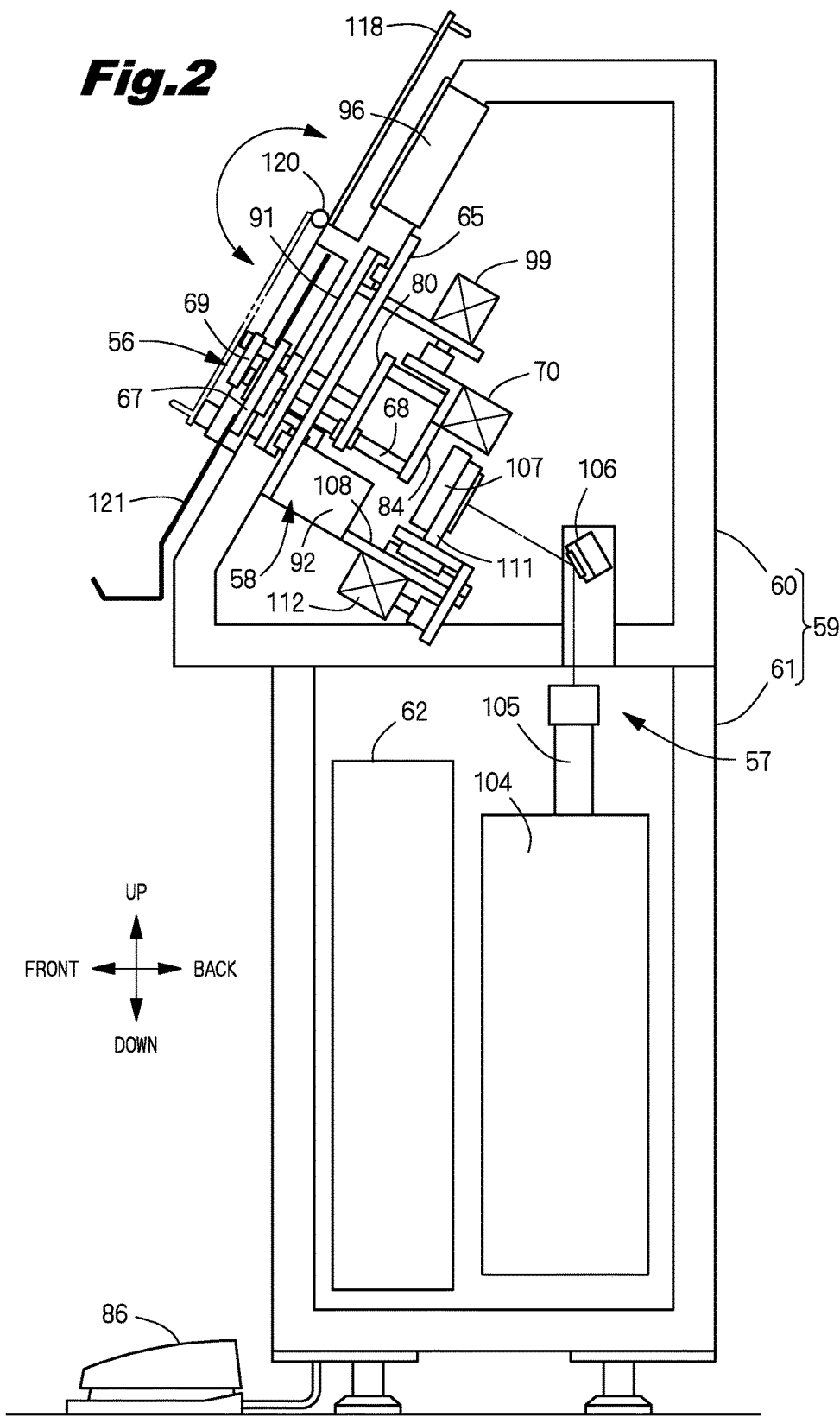
FIG. 2 is a side view of a schematic configuration of the sealing apparatus according to the invention.
Figure 3:
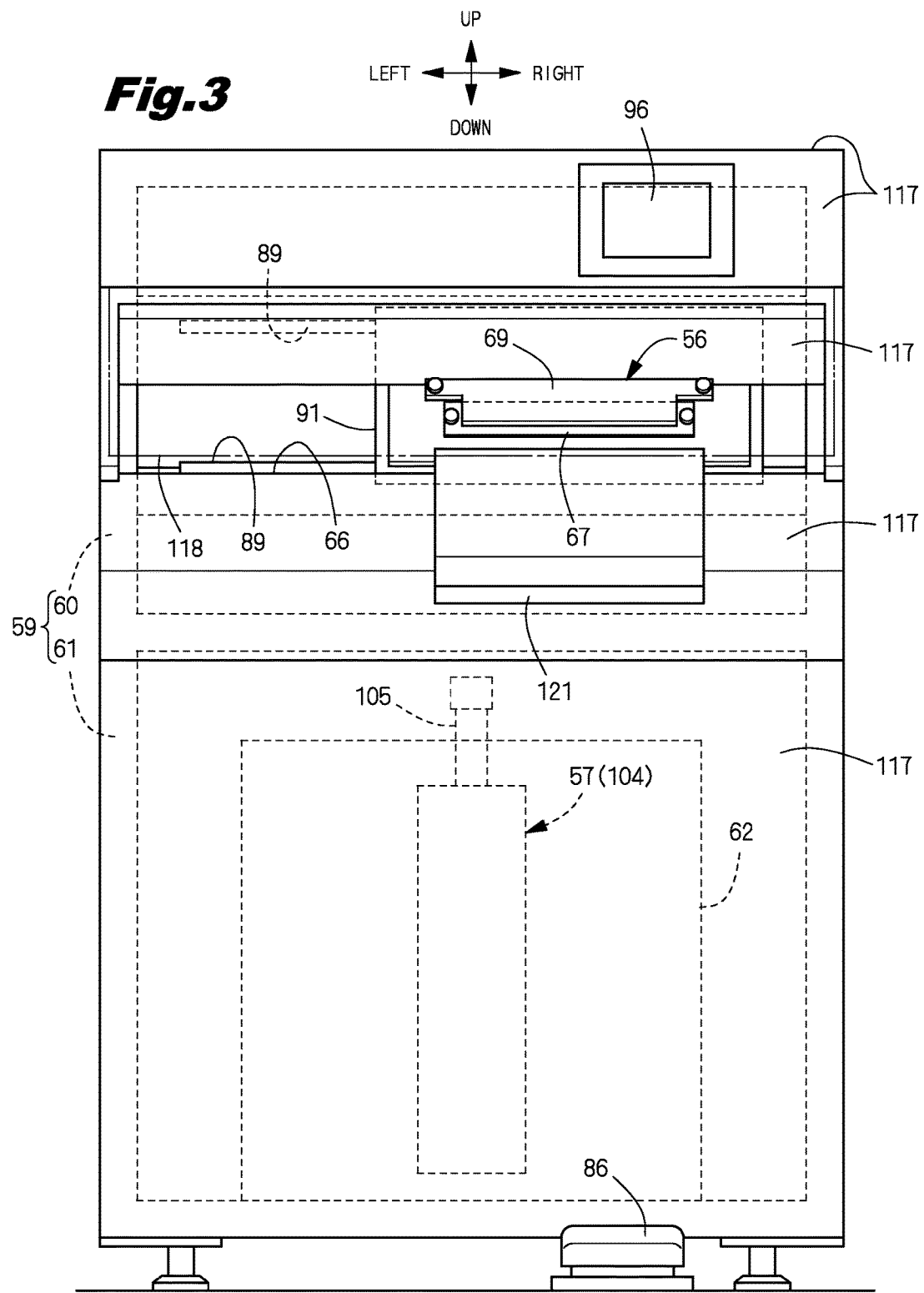
FIG. 3 is a front view of the sealing apparatus according to the invention.

As described above, the movable pinching block 69 is operated forward and backward by the solenoid 70 and the springs 71 to be displaced between a clamping attitude in which the movable pinching block 69 comes in contact with the heat radiator holder 75 from outside and a standby attitude in which the movable pinching block 69 moves forward away from the heat radiator holder 75. In a normal state, the movable pinching block 69 receives biasing forces of the springs 71 and is kept in the standby attitude. As shown in FIG. 1, the solenoid 70 is mounted to an inner base 84 fixed to back ends of the guide shafts 68 and an operating shaft 85 continuous from a moving core of the solenoid 70 is fixed to a center in the left-right direction of the movable base 80. As shown in FIGS. 2 and 3, a foot switch (switch) 86 for actuating the solenoid 70 is provided on a floor face in front of the sealing apparatus. If the switch 86 is stepped on, the moving core is attracted to an inside of the solenoid 70 and, in this way, it is possible to switch the movable pinching block 69 into the clamping attitude against the biasing forces of the springs 71. This clamping attitude is maintained until the sealing treatment is finished. If the foot switch 86 is stepped on after the sealing treatment is finished, the movable pinching block 69 is returned into the standby attitude by the springs 71.

As described above, if the movable pinching block 69 is supported to be able to slide forward and backward with respect to the guide shafts 68 of the fixed pinching block 67, the movable pinching block 69 can smoothly move forward and backward with respect to the fixed pinching block 67 and it is possible to obtain high parallelism between pinching faces of both the pinching blocks 67 and 69. Moreover, if the solenoid 70 is provided to the inner base 84 fixed to the guide shafts 68, the movable pinching block 69 can be operated forward and backward by the solenoid 70 with a simpler structure and the sealed portion 55 can be reliably clamp-fixed between both the fixed and movable pinching blocks 67 and 69.

The scanning structure 58 is formed by the scanning base 65, guide rails (guide bodies) 89 provided to upper and lower positions of a front edge of the scanning window 66 of the scanning base 65, four slide bodies 90 in total guided and supported by the guide rails 89 to be able to slide leftward and rightward, the laterally-long rectangular frame clamping table 91 fixed to the slide bodies 90, a gate-shaped inner frame 92 fixed to a back face of a lower portion of the scanning base 65, an electric slider (scanning actuator) 93 which is long in the left-right direction and fixed to the inner frame 92, and the like. The clamping table 91 is formed in a laterally-long rectangular frame shape and the table 91 and a moving table 94 of the electric slider 93 are connected by an interlocking arm 95 in an inverted L shape. By actuating the electric slider 93, the bag clamping device 56 can be moved while scanning from one end of the scanning window 66 to the other end. At this time, a moving stroke of the bag clamping device 56 by the scanning structure 58 is set to be sufficiently longer than a left-right width of the sealed portion 55 of the cryopreservation bag. A touch-screen display 96 is provided at a right upper corner of a front face of the frame 59 and it is possible to actuate the electric slider 93 to simultaneously cause the laser device 57 to radiate the infrared laser beam by touching a start button displayed on the display 96.

In order to cause the bag clamping device 56 to scan upward and downward, a vertical scanning structure is provided inside the frame 59. The vertical scanning structure is formed by a vertically-long guide rail (vertical guide) 97 fixed to the clamping table 91, vertical sliders 98 supported by the guide rail 97 to be able to slide in reciprocating manners, a servomotor (vertical scanning actuator) 99 for operating the bag clamping device 56 upward and downward via the above-described inner base 84, and the like. As shown in FIG. 4, the block base 73 of the fixed pinching block 67 is fixed to the paired left and right vertical sliders 98. The servomotor 99 is disposed on an upper face of an actuator base 100 fixed to an inner face of an upper portion of the clamping table 91 and rotation power of the servomotor 99 is converted into reciprocating motion by a threaded shaft 101 and an internal thread body 102 fixed to the inner base 84 to move the bag clamping device 56 upward and downward.

In FIG. 2, the laser device 57 is a commercially available carbon dioxide laser unit and formed by a vertically-long rectangular box-shaped laser oscillator 104, a radiating pipe 105 protruding from an upper end of the laser oscillator 104, a deflecting mirror 106 for deflecting the laser beam output from the laser oscillator 104 into a diagonally upward direction, a condensing lens 107 for throttling the laser beam and radiating the laser beam toward the heat radiator 74, and the like. In order to adjust a focus position of the condensing lens 107, a focus adjustment structure is provided behind the inner frame 92.

The focus adjustment structure is formed by a lens base 108 supported by the inner frame 92, paired left and right lens guides 109 fixed to the lens base 108, a forward-backward slider 110 supported to be able to slide forward and backward in a reciprocating manner by the respective lens guides 109, a lens holder 111 fixed to the forward-backward slider 110 and supporting the condensing lens 107, a servomotor (focus adjustment actuator) 112 for operating the lens holder 111 forward and backward, and the like. The servomotor 112 is disposed on a lower face side of the lens base 108 and rotation power of the servomotor 112 is converted into reciprocating motion by a threaded shaft 113 and an internal thread body 114 fixed to the lens holder 111 to adjust the focus position of the condensing lens 107.

In the process of sealing the cryopreservation bag, the infrared laser emitted from the laser device 57 may leak and all peripheral side faces and an upper face of the frame 59 are covered with protective barriers 117 in order to avoid exposure to the leaking laser light. Moreover, in order to prevent leakage of the infrared laser radiated toward the sealed portion 55, a protective cover 118 is provided to a front face of the bag clamping device 56 and supported to be swung open and close by a bracket 119 and hinges 120 provided to the frame 59 (see FIGS. 1 and 2). In attaching and detaching the cryopreservation bag to and from the bag clamping device 56, the protective cover 118 can be swung open upward and retained in an open position as shown in FIG. 2. In FIGS. 1 and 2, reference numeral 121 designates a drop prevention plate for preventing a drop of the cryopreservation bag after the sealing treatment onto a floor face by mistake.

Figure 6:
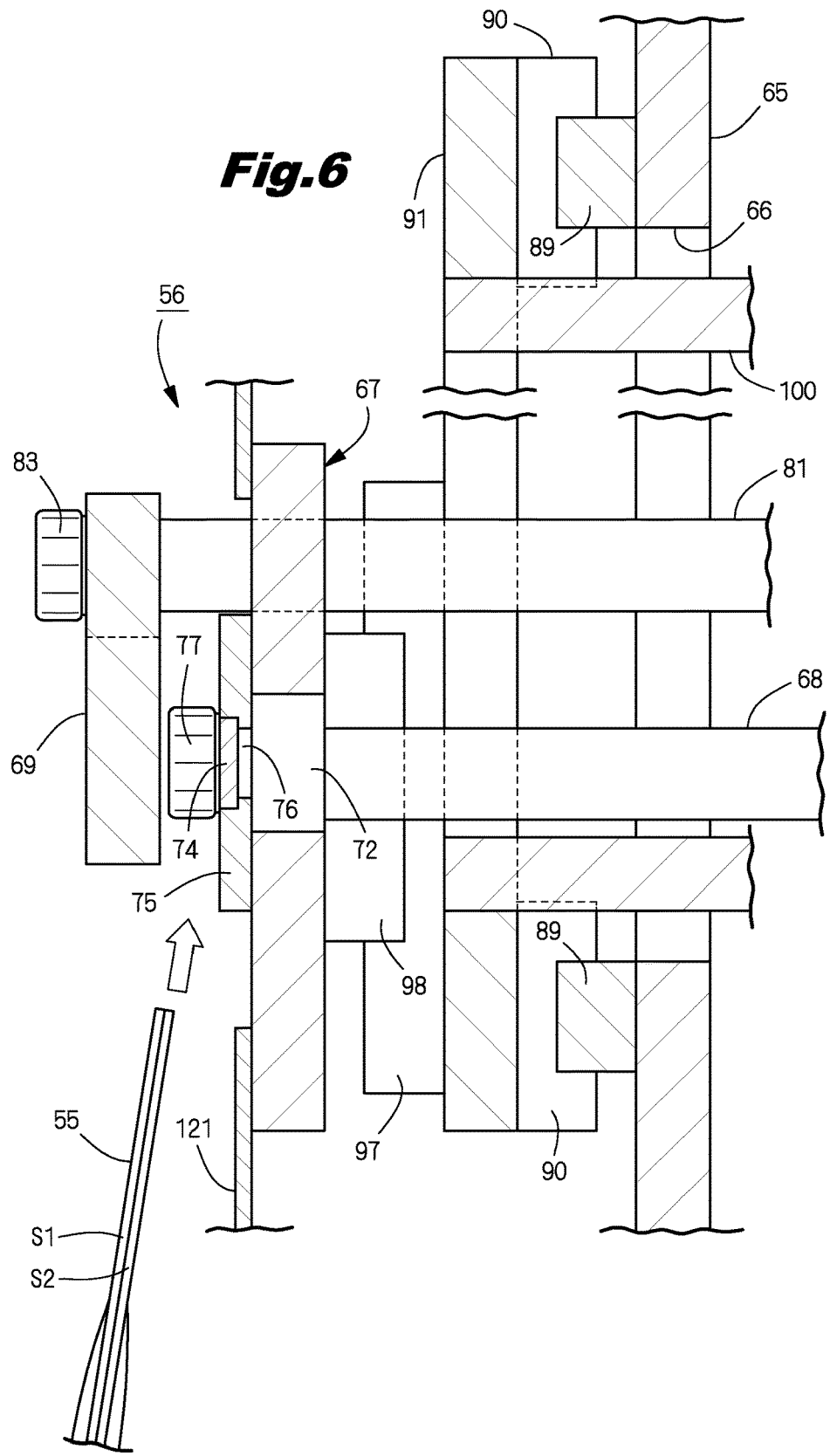
FIG. 6 is a vertical sectional side view showing a procedure for attaching a sealed portion to the bag clamping device.

A sealing procedure for the cryopreservation bag will be described below. Prior to the sealing treatment, preparation for radiation of the infrared laser is made by carrying out adjustment of the laser device 57 and the focus adjustment of the condensing lens 107 and the bag clamping device 56 is moved to a home position shown in FIG. 3. Moreover, the bag clamping device 56 is brought into a standby state by setting welding conditions while checking display on the display 96. The biological tissue is filled into the housing portion 2 of the cryopreservation bag and the bag is evacuated so that the sealed portion 55 is flattened into a sheet shape. In this state, as shown in FIG. 6, the sealed portion 55 is inserted between the movable pinching block 69 and the heat radiator 74 and positioned. In this state, the foot switch 86 is stepped on and the solenoid 70 operates the movable pinching block 69 backward to bring the movable pinching block 69 into the clamping attitude.

Figure 7:
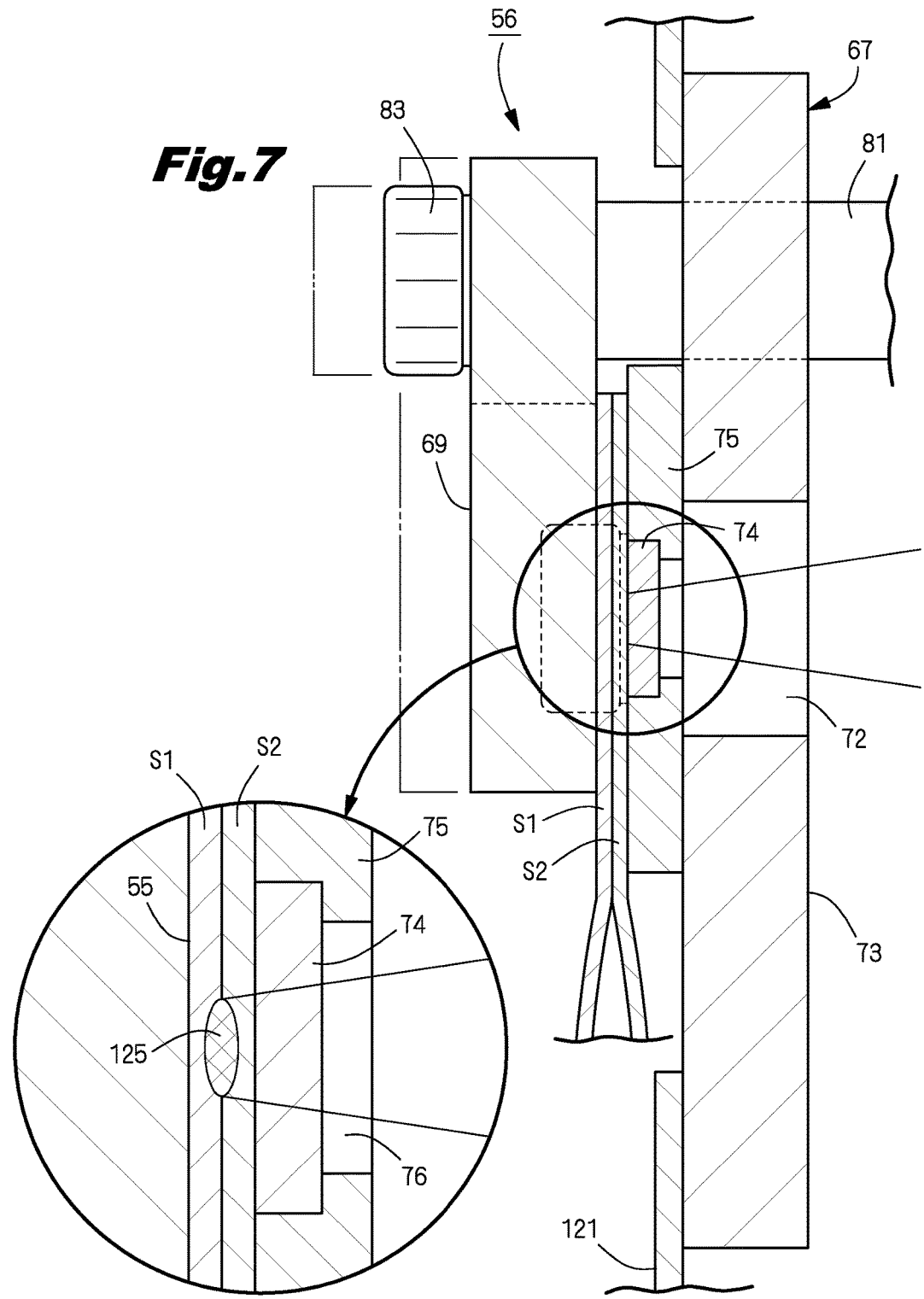
FIG. 7 is a vertical sectional side view showing a state in which the sealed portion is clamped.

In the state in which the movable pinching block 69 is brought into the clamping attitude, as shown in FIGS. 7 and 8, a most portion of the sealed portion 55 of the cryopreservation bag is pinched and fixed between the movable pinching block 69 and the heat radiator 74. In this state, if the start button displayed on the display 96 is touched, the infrared laser beam is radiated from the laser device 57 toward the heat radiator 74. Simultaneously, the electric slider 93 is actuated to feed the bag clamping device 56 from the home position toward a left side in FIG. 3 at a constant speed to thereby form the seal bead 125.

At this time, because the infrared laser passes through the heat radiator 74, the heat radiator 74 does not absorb the infrared laser to generate heat. Moreover, although welding heat is conducted to a periphery of a position where the bead is formed when the seal bead 125 is formed, the welding heat which has reached to a back surface of the sealed portion 55 is absorbed by the heat radiator 74 with high heat conductivity and diffused. Similarly, the welding heat which has reached a front surface of the sealed portion 55 is absorbed by the movable pinching block 69 with high heat conductivity and diffused. Therefore, at the sealed portion 55, only the interface between the fluorine-based resin sheets S1 and S2 is welded as shown in an enlarged view in FIG. 7.

When the seal bead 125 is formed from one end of the sealed portion 55 to the other end, the radiation of the infrared laser and the feeding operation by the scanning structure 58 are stopped temporarily. In this state, the servomotor 99 of the vertical scanning structure is actuated to move the bag clamping device 56 upward (or downward) a distance corresponding to a spot diameter of the infrared laser beam. Moreover, while the scanning structure 58 is actuated to feed the bag clamping device 56 toward a right side in FIG. 3, the infrared laser beam is radiated to the sealed portion 55 to form the return seal bead 125 below (or above) the outgoing seal bead 125. When the bag clamping device 56 returns to the home position, as shown in FIG. 9, the two seal beads 125 extending across the sealed portion 55 in the outgoing and returning manners are formed. Then, if the foot switch 86 is stepped on while the cryopreservation bag is supported with a hand, clamping of the sealed portion 55 by the bag clamping device 56 is released and the cryopreservation bag can be taken out. The vertical scanning structure may be returned into an initial state when the bag clamping device 56 returns to the home position or the bag clamping device 56 may be moved in a reverse direction from the previous direction after the return seal bead 125 is formed. By repeating the above-described procedure, it is possible to properly form the seal beads 125 at the sealed portions 55 of the cryopreservation bags.

According to the sealing apparatus formed as described above, it is possible to automatically seal the inlet/outlet 3 of the cryopreservation bag formed by the fluorine-based resin sheets S1 and S2 by moving the movable pinching block 69 with the clamp actuator 70 to clamp the sealed portion 55 and then actuating the scanning structure 58 and the laser device 57. The sealing operation of the sealed portion 55 of the cryopreservation bag is carried out by users on the site such as doctors and medical technologists. Because a series of welding operations is carried out automatically after the sealed portion 55 is clamped by the bag clamping device 56, it is possible to safely and properly carry out the sealing treatment of the cryopreservation bag. Moreover, the sealing treatment is always carried out automatically under constant conditions and therefore there is no variation between welding results. As a result, it is possible to provide the sealing apparatus for the cryopreservation bag, with which anyone can easily carry out the sealing treatment which can stably impart the high sealing function.

Because the movable pinching block 69 and the fixed pinching block 67 face the outer face of the scanning window 66, it is possible to easily attach and detach the sealed portion 55 to and from the bag clamping device 56 on the outer face of the scanning window 66 facing a free space. Therefore, it is possible to appropriately clamp the sealed portion 55 with the bag clamping device 56 while checking a position and an attitude of the cryopreservation bag or it is possible to reliably retrieve the cryopreservation bag after the welding operation is finished, which improves overall usability of the sealing apparatus.

If the movable pinching block 69 is supported to be able to slide forward and backward with respect to the guide shafts 68 of the fixed pinching block 67, the movable pinching block 69 can be smoothly moved forward and backward with respect to the fixed pinching block 67 and the parallelism between the pinching faces of both the pinching blocks 67 and 69 can be enhanced. Moreover, if the clamp actuator 70 is provided to the inner base 84 fixed to the guide shafts 68, the movable pinching block 69 can be operated forward and backward by the clamp actuator 70 with the simpler structure and the sealed portion 55 can be reliably clamp-fixed between both the fixed and movable pinching blocks 67 and 69.

The movable pinching block 69 is detachably mounted to the block support shafts 81 by the first screw bodies 83 and the heat radiator holder 75 is detachably mounted to the block base 73 by the second screw bodies 77. According to the sealing apparatus, the movable pinching block 69 and the heat radiator holder 75 can be detached from the block support shafts 81 and the block base 73 as necessary and the movable pinching block 69 and the heat radiator holder 75 to which the biological tissue may be attached can be sterilized. Therefore, it is possible to facilitate hygiene control of the movable pinching block 69, the heat radiator 74, and the heat radiator holder 75 to safely carry out the sealing treatment of the sealed portion 55 of the cryopreservation bag from a hygiene perspective.

Although the seal beads 125 are formed continuously from one end to the other end of the sealed portion 55 in the above embodiment, this is not necessary. It suffices if the seal beads 125 are formed across at least the inlet/outlet 3. Although the two seal beads 125 are formed by forming the return seal bead 125 beside the outgoing seal bead 125 in the above embodiment, the sealed portion 55 may be sealed with only any one of the outgoing and return seal beads 125. If necessary, it is possible to actuate the vertical scanning actuator 99 in synchronization with the feeding operation of the scanning structure 58 to thereby form the seal beads 125 in continuous wave patterns or sawtooth patterns.

FIGS. 14 and 15 show a variation of the cryopreservation bag. Here, an infrared laser beam is radiated to two layered transparent fluorine-based resin sheets S1 and S2 to form paired left and right outline beads 1 in an interface between both the sheets S1 and S2 to thereby form a housing portion 132 for housing biological tissue, a vent hole 133 continuous with the housing portion 2, and an air bleed portion 134 continuous with the vent hole 133 in an area between both the sheets S1 and S2 and between the outline beads 1. A portion of the air bleed portion 134 near an end portion is sealed with a first seal bead 135. The vent hole 133 is formed at a center in a left-right direction of bag walls.

The housing portion 132 is defined by the paired left bead portion 136 and right bead portion 137 and shoulder bead portions 138 inclined in a tapered shape from both the bead portions 136 and 137 toward the vent hole 133, upper end portions of both the left and right bead portions 136 and 137 intersect a short-side portion of the fluorine-based resin sheets S1 and S2 at right angles, and a filling hole 139 through which the biological tissue is filled into the housing portion 132 is open between both the bead portions 136 and 137. The air bleed portion 134 is formed in a funnel shape. As shown in FIG. 15, a left-right width of the air bleed portion 134 is set to be sufficiently larger than a left-right width of the vent hole 133 and a left-right width of the housing portion 132 is set to be even larger than the left-right width of the air bleed portion 134.

The cryopreservation bag formed as described above is sealed after the biological tissue such as blood is filled into the housing portion 132 and a series of operations is carried out by the following procedure.

First, as shown in FIG. 15, the filling hole 139 is oriented upward and opened and then the biological tissue is filled into the housing portion 2 from the filling hole 139 (step 1).

At this time, the biological tissue can be filled from the wide-open filling hole 139 having the same width as the housing portion 132 and therefore the biological tissue can be filled or poured into the housing portion 2 easily and quickly. Next, by bringing the bag walls on a side of the filling hole 139 into close contact with each other while pushing air out of the housing portion 132, the side of the filling hole 139 of the cryopreservation bag filled with the biological tissue is sealed with second seal beads 140 as shown in FIG. 16 (step 2). The housing portion 2 in this state includes a small amount of air in many cases. In order to release the air, the bag walls are cut along a cutoff line 141 along the first seal bead 135 to separate and remove the bag walls including the first seal bead 140 to form an air bleed opening 142 near the end portion of the air bleed portion 4 (step 3).

The cryopreservation bag in which the air bleed opening 142 is formed is erected and held with the air bleed portion 134 positioned above the housing portion 132. Next, a liquid level is raised by pushing the biological tissue in the housing portion 132 out from the vent hole 133 into the air bleed portion 134 and air is released from the air bleed opening 142 while the bag walls of the air bleed portion 134 are brought into close contact with each other (step 4). At this time, all the air in the air bleed portion 134 can be reliably exhausted by releasing the air from the air bleed opening 142 while bringing the bag walls of the wide air bleed portion 134 into close contact with each other. Furthermore, a provisional sealed portion 143 can be formed by bringing the bag walls between the air bleed portion 134 and an upper portion of the housing portion 132 into close contact with each other. By sealing the provisional sealed portion 143 with a third seal bead 144 in this state (step 5), it is possible to seal only the biological tissue in the housing portion 132.

According to the above-described cryopreservation bag, the biological tissue can be filled from the wide open filling hole 139 having the large width and therefore the biological tissue can be filled or poured into the housing portion 132 easily and quickly. Moreover, the liquid level can be raised by pushing the biological tissue in the housing portion 2 out from the vent hole 133 into the wide air bleed portion 134 and the air can be released from the air bleed opening 142 while the bag walls of the air bleed portion 134 are brought into close contact with each other. Therefore, it is possible to easily and quickly exhaust the air trapped in the housing portion 132. The first seal bead 135 can be formed in a manufacturing process of the cryopreservation bag while the second seal beads 140 and the third seal bead 144 are formed by using the sealing apparatus.

Besides the above-described variation, the clamp actuator 70 does not necessarily have to be the solenoid but may be an electric slider, an electric cylinder, a liner actuator, or the like. Similarly, the scanning actuator 93 may be formed by an electric cylinder, a linear actuator, or the like besides the electric slider. Furthermore, the vertical adjustment actuator 99 and the focus adjustment actuator 112 may be formed by an electric slider, an electric cylinder, a linear actuator, or the like. The laser oscillator 104 may be disposed in such an attitude to be long in a lateral direction or a front-back direction. Although the sealing apparatus according to the invention is especially suitable to the sealing treatment of the sealed portion of the cryopreservation bag formed by the fluorine-based resin sheets S1 and S2, the sealing treatment can be equally carried out for a cryopreservation bag formed by resin sheets other than the fluorine-based resin sheets.

Therefore, the cryopreservation bag to be sealed is not limited to the bag formed by the fluorine-based resin sheets S1 and S2.

REFERENCE SIGNS LIST

55: Sealed portion
56: Bag clamping device
57: Laser device
58: Scanning structure
59: Frame
65: Scanning base
67: Fixed pinching block
69: Movable pinching block
70: Clamp actuator (solenoid)
74: Heat radiator
91: Clamping table
93: Scanning actuator (electric slider)
107: Condensing lens
125: Seal bead

The invention claimed is:

1. A sealing apparatus for a cryopreservation bag, the apparatus comprising:
 a bag clamping device (56) for pinching and fixing a sealed portion (55) of the cryopreservation bag, the sealed portion (55) having a front surface and a back surface;
 a laser device (57) for radiating an infrared laser beam toward the back surface of the sealed portion (55) when the sealed portion (55) is pinched and fixed by the bag clamping device (56);
 a scanning structure (58) for moving any one of the bag clamping device (56) and the laser device (57); and
 a frame (59) for supporting the respective members (56 to 58),
 wherein the bag clamping device (56) includes a fixed pinching block (67) supported by a scanning base (65) fixed to the frame (59), a movable pinching block (69) supported by a guide shaft (68) provided to the fixed pinching block (67) to be able to come in contact with and move away from the fixed pinching block (67), and a clamp actuator (70) for bringing the movable pinching block (69) into contact with and moving the movable pinching block (69) away from the fixed pinching block (67),
 the laser device (57) includes a laser oscillator (104) and a condensing lens (107) for condensing the infrared laser beam, the laser device being configured to radiate the infrared laser beam to the sealed portion (55) of the cryopreservation bag to form a seal bead (125),
 the fixed pinching block (67) includes a block base (73) in which a radiation window (72) for the infrared laser beam is open, a heat radiator (74) made of solid material with high infrared transmissivity and high heat conductivity, and a heat radiator holder (75) mounted to the block base (73) to support the heat radiator (74) so that the heat radiator (74) faces the radiation window (72), the heat radiator being configured to allow the infrared laser beam to pass therethrough, and
 the heat radiator (74), the heat radiator holder (75), and the movable pinching block (69) are configured to pinch and fix the sealed portion (55) and the scanning structure (58) is configured to move any one of the bag clamping device (56) and the laser device (57) at the time of radiating the infrared laser beam to the sealed portion (55) of the cryopreservation bag to form a seal bead (125) crossing an inlet/outlet (3) at the sealed portion (55),
 the heat radiator (74) is configured to absorb and diffuse welding heat which is generated by the infrared laser beam when forming the seal bead (125) and which reaches the back surface of the sealed portion (55), and
 the movable pinching block (69) is configured to absorb and diffuse the welding heat which reaches the front surface of the sealed portion (55).

2. The sealing apparatus for the cryopreservation bag according to claim 1,
 wherein the scanning structure (58) includes a guide body (89) provided to the scanning base (65), a slide body (90) guided and supported by the guide body (89) to be able to slide leftward and rightward, a clamping table (91) fixed to the slide body (90), and a scanning actuator (93) provided to the scanning base (65) to reciprocate the clamping table (91) leftward and rightward,
 the block base (73) of the fixed pinching block (67) is supported by the clamping table (91), and
 the infrared laser beam is radiated from the radiation window (72) to the sealed portion (55) to form the seal bead (125) crossing the inlet/outlet (3) at the sealed portion (55) while the bag clamping device (56) is moved by the scanning structure (58).

3. The sealing apparatus for the cryopreservation bag according to claim 2,
 wherein the scanning base (65) is fixed to an upper frame (60) forming the frame (59),
 a scanning window (66) for allowing leftward and rightward movements of the bag clamping device (56) is open in the scanning base (65), the movable pinching block (69) and the fixed pinching block (67) face an outer face of the scanning window (66), and
 the sealed portion (55) of the cryopreservation bag can be attached to and detached from the bag clamping device (56) on the outer face of the scanning window (66).

4. The sealing apparatus for the cryopreservation bag according to claim 3,
 wherein the movable pinching block (69) is supported by paired left and right sliders (79) supported by the guide shaft (68) to be able to slide forward and backward in a reciprocating manner, a plate-shaped movable base (80) fixed to and supported by both the sliders (79), and paired left and right block support shafts (81) fixed to left and right positions of a front face of the movable base (80),
 the clamp actuator (70) for operating the movable pinching block (69) forward and backward via the movable base (80) and the block support shafts (81) is provided to an inner base (84) fixed to the guide shaft (68), and
 the sealed portion (55) of the cryopreservation bag can be clamp-fixed by both the fixed and movable pinching blocks (67, 69) by operating the movable pinching block (69) with the clamp actuator (70) in a state in which the sealed portion (55) is brought in contact with an outer face of the heat radiator (74) of the fixed pinching block (67).

5. The sealing apparatus for the cryopreservation bag according to claim 4,
 wherein the movable pinching block (69) is detachably mounted to a block support shaft (81) by a first mounting member (83), the heat radiator holder (75) is detachably mounted to the block base (73) by a second mounting member (77), and the movable pinching block (69) and the heat radiator holder (75) can be detached from the block support shaft (81) and the block base (73) and sterilized.

6. The sealing apparatus for the cryopreservation bag according to claim 5, wherein a focus adjustment structure for adjusting a focus position of the condensing lens (107) is provided inside the frame (59), the focus adjustment structure includes a lens base (108) supported by an inner frame (92) fixed to the scanning base (65), a lens guide (109) fixed to the lens base (108), a forward-backward slider (110) supported by the lens guide (109) to be able to slide forward and backward, a lens holder (111) fixed to the forward-backward slider (110) to support the condensing lens (107), and a focus adjustment actuator (112) for operating the lens holder (111) forward and backward, and the focus position of the condensing lens (107) can be adjusted according to a thickness of the sealed portion (55) pinched and fixed by the bag clamping device (56).

7. The sealing apparatus for the cryopreservation bag according to claim 6, wherein a vertical scanning structure for adjusting a vertical position of the bag clamping device (56) is provided inside the frame (59), the vertical adjustment structure includes a vertical guide (97) fixed to the clamping table (91), a vertical slider (98) fixed to the block base (73) and supported by the vertical guide (97) to be able to slide vertically, an actuator base (100) fixed to the clamping table (91), and a vertical scanning actuator (99) disposed between the base (100) and the inner base (84) to operate the bag clamping device (56) vertically, and a position of the sealed portion (55) where the seal bead (125) is formed can be changed by vertically operating the bag clamping device (56) with the vertical scanning structure.

8. The sealing apparatus for the cryopreservation bag according to claim 7, wherein a moving stroke of the bag clamping device (56) by the scanning structure (58) is set to be larger than a left-right width of the sealed portion (55) of the cryopreservation bag and the seal bead (125) can be formed across the sealed portion (55) of the cryopreservation bag from one end to the other end.

9. The sealing apparatus for the cryopreservation bag according to claim 8, wherein an outer face of the frame (59) is covered with a protective barrier (117) for preventing exposure to infrared laser leaking from the laser device (57) and a protective cover (118) for preventing exposure to the infrared laser is provided to an outer face of the bag clamping device (56) to be able to open and close.

10. The sealing apparatus for the cryopreservation bag according to claim 2, wherein the movable pinching block (69) is supported by paired left and right sliders (79) supported by the guide shaft (68) to be able to slide forward and backward in a reciprocating manner, a plate-shaped movable base (80) fixed to and supported by both the sliders (79), and paired left and right block support shafts (81) fixed to left and right positions of a front face of the movable base (80), the clamp actuator (70) for operating the movable pinching block (69) forward and backward via the movable base (80) and the block support shafts (81) is provided to an inner base (84) fixed to the guide shaft (68), and the sealed portion (55) of the cryopreservation bag can be clamp-fixed by both the fixed and movable pinching blocks (67, 69) by operating the movable pinching block (69) with the clamp actuator (70) in a state in which the sealed portion (55) is brought in contact with an outer face of the heat radiator (74) of the fixed pinching block (67).

11. The sealing apparatus for the cryopreservation bag according to claim 2, wherein the movable pinching block (69) is detachably mounted to a block support shaft (81) by a first mounting member (83), the heat radiator holder (75) is detachably mounted to the block base (73) by a second mounting member (77), and the movable pinching block (69) and the heat radiator holder (75) can be detached from the block support shaft (81) and the block base (73) and sterilized.

12. The sealing apparatus for the cryopreservation bag according to claim 2, wherein a focus adjustment structure for adjusting a focus position of the condensing lens (107) is provided inside the frame (59), the focus adjustment structure includes a lens base (108) supported by an inner frame (92) fixed to the scanning base (65), a lens guide (109) fixed to the lens base (108), a forward-backward slider (110) supported by the lens guide (109) to be able to slide forward and backward, a lens holder (111) fixed to the forward-backward slider (110) to support the condensing lens (107), and a focus adjustment actuator (112) for operating the lens holder (111) forward and backward, and the focus position of the condensing lens (107) can be adjusted according to a thickness of the sealed portion (55) pinched and fixed by the bag clamping device (56).

13. The sealing apparatus for the cryopreservation bag according to claim 2, wherein a vertical scanning structure for adjusting a vertical position of the bag clamping device (56) is provided inside the frame (59), the vertical adjustment structure includes a vertical guide (97) fixed to the clamping table (91), a vertical slider (98) fixed to the block base (73) and supported by the vertical guide (97) to be able to slide vertically, an actuator base (100) fixed to the clamping table (91), and a vertical scanning actuator (99) disposed between the base (100) and the inner base (84) to operate the bag clamping device (56) vertically, and a position of the sealed portion (55) where the seal bead (125) is formed can be changed by vertically operating the bag clamping device (56) with the vertical scanning structure.

14. The sealing apparatus for the cryopreservation bag according to claim 1, wherein a moving stroke of the bag clamping device (56) by the scanning structure (58) is set to be larger than a left-right width of the sealed portion (55) of the cryopreservation bag and the seal bead (125) can be formed across the sealed portion (55) of the cryopreservation bag from one end to the other end.

15. The sealing apparatus for the cryopreservation bag according to claim 1, wherein an outer face of the frame (59) is covered with a protective barrier (117) for preventing exposure to infrared laser leaking from the laser device (57) and a protective cover (118) for preventing exposure to the infrared laser is provided to an outer face of the bag clamping device (56) to be able to open and close.

16. A sealing apparatus for a cryopreservation bag, the apparatus comprising: a bag clamping device (56) for pinching and fixing a sealed portion (55) of the cryopreservation bag; a laser device (57) for radiating an infrared laser beam toward the sealed portion (55) pinched and fixed by the bag clamping device (56); a scanning structure (58) for moving any one of the bag clamping device (56) and the laser device (57); and a frame (59) for supporting the respective members (56 to 58), wherein the bag clamping device (56) includes a fixed pinching block (67) supported by a scanning base (65) fixed to the frame (59), a movable pinching block (69) supported by a guide shaft (68) provided to the fixed pinching block (67) to be able to come in contact with and move away from the fixed pinching block (67), and a clamp actuator (70) for bringing the movable pinching block (69) into contact with and moving the movable pinching block (69) away from the fixed pinching block (67), the laser device (57) includes a laser oscillator (104) and a condensing lens (107) for condensing the infrared laser beam radiated from the laser oscillator (104) toward the sealed portion (55) of the cryopreservation bag, the fixed pinching block (67) includes a block base (73) in which a radiation window (72) for the infrared laser beam is open, a heat radiator (74) made of solid material with high infrared transmissivity and high heat conductivity, and a heat radiator holder (75) mounted to the block base (73) to support the heat radiator (74) so that the heat radiator (74) faces the radiation window (72), and the heat radiator (74), the heat radiator holder (75), and the movable pinching block (69) are configured to pinch and fix the sealed portion (55) and the scanning structure (58) is configured to move any one of the bag clamping device (56) and the laser device (57) at the time of radiating the infrared laser beam to the sealed portion (55) of the cryopreservation bag to form a seal bead (125) crossing an inlet/outlet (3) at the sealed portion (55), the scanning structure (58) includes a guide body (89) provided to the scanning base (65), a slide body (90) guided and supported by the guide body (89) to be able to slide leftward and rightward, a clamping table (91) fixed to the slide body (90), and a scanning actuator (93) provided to the scanning base (65) to reciprocate the clamping table (91) leftward and rightward, the block base (73) of the fixed pinching block (67) is supported by the clamping table (91), and the infrared laser beam is radiated from the radiation window (72) to the sealed portion (55) to form the seal bead (125) crossing the inlet/outlet (3) at the sealed portion (55) while the bag clamping device (56) is moved by the scanning structure (58).

* * * * *